(12) United States Patent
Kim et al.

(10) Patent No.: US 10,702,440 B2
(45) Date of Patent: Jul. 7, 2020

(54) MOTION ASSISTANCE APPARATUS AND METHOD OF CONTROLLING THE SAME

(71) Applicant: Samsung Electronics Co., Ltd., Suwon-si, Gyeonggi-do (KR)

(72) Inventors: Kyung-Rock Kim, Yongin-si (KR); Youngjin Park, Seoul (KR); Youngbo Shim, Seoul (KR); Bokman Lim, Yongin-si (KR); Jun-Won Jang, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 947 days.

(21) Appl. No.: 15/012,528

(22) Filed: Feb. 1, 2016

(65) Prior Publication Data

US 2017/0049658 A1 Feb. 23, 2017

(30) Foreign Application Priority Data

Aug. 17, 2015 (KR) ........................ 10-2015-0115513

(51) Int. Cl.
*A61H 3/00* (2006.01)
*A61F 2/68* (2006.01)
(Continued)

(52) U.S. Cl.
CPC ................. *A61H 3/00* (2013.01); *A61F 2/68* (2013.01); *A61H 1/0244* (2013.01);
(Continued)

(58) Field of Classification Search
CPC ...... A61H 1/00; A61H 1/0255; A61H 1/0262; A61H 3/00; A61H 2201/1215;
(Continued)

(56) References Cited

U.S. PATENT DOCUMENTS 7,744,552 B1 6/2010 Babcock
7,880,552 B2 2/2011 Yasuhara et al.
(Continued)

FOREIGN PATENT DOCUMENTS

EP 1932567 A1 6/2008
EP 1 958 607 A1 8/2008
(Continued)

OTHER PUBLICATIONS

Partial European Search Report dated Dec. 12, 2016 by the European Patent Office for corresponding EP Patent Application No. 16163528.9.

(Continued)

*Primary Examiner* — Quang D Thanh
(74) *Attorney, Agent, or Firm* — Harness, Dickey and Pierce, P.L.C.

(57) ABSTRACT

A motion assistance apparatus including a fixing module to be attached to a waist of a user, a driving module provided in the fixing module to provide a torque to assist a motion of the user, a supporting module connected to the driving module to support a portion of a circumference of a leg of the user, and a controller configured to control the driving module to provide a torque to maintain a close contact between the supporting module and the leg of the user while the user is not walking.

16 Claims, 24 Drawing Sheets

(51) Int. Cl.
*A61H 1/02* (2006.01)
*A61F 2/50* (2006.01)

(52) U.S. Cl.
CPC .... *A61F 2002/5007* (2013.01); *A61H 1/0255* (2013.01); *A61H 1/0262* (2013.01); *A61H 2003/007* (2013.01); *A61H 2201/12* (2013.01); *A61H 2201/1215* (2013.01); *A61H 2201/164* (2013.01); *A61H 2201/165* (2013.01); *A61H 2201/1628* (2013.01); *A61H 2201/1676* (2013.01); *A61H 2201/50* (2013.01); *A61H 2201/5061* (2013.01); *A61H 2201/5069* (2013.01); *A61H 2201/5071* (2013.01)

(58) Field of Classification Search
CPC ...... A61H 2201/1628; A61H 2201/164; A61H 2201/165; A61H 2201/1676; A61H 2201/50; A61H 2201/5061; A61H 2201/5069; A61H 2201/5071; A61H 2205/106; A61H 2205/108; A61H 1/0244; A61H 2201/12; A61H 2003/007; A61F 2/68; A61F 5/0102; A61F 2002/5007; B25J 9/00
See application file for complete search history.

(56) References Cited

U.S. PATENT DOCUMENTS

| | | | | |
|---|---|---|---|---|
| 8,366,788 | B2* | 2/2013 | Moser | A61B 5/112 600/587 |
| 2005/0177080 | A1* | 8/2005 | Yasuhara | A61B 5/112 602/16 |
| 2009/0312682 | A1* | 12/2009 | Hirata | A61F 5/0193 602/23 |
| 2010/0121232 | A1* | 5/2010 | Sankai | A61H 3/008 601/23 |
| 2011/0266323 | A1* | 11/2011 | Kazerooni | B25J 9/0006 224/575 |
| 2012/0215140 | A1* | 8/2012 | Hirata | A61H 1/0244 601/35 |
| 2014/0024978 | A1* | 1/2014 | Killian | A61H 1/0244 601/33 |
| 2014/0330431 | A1* | 11/2014 | Hollander | B25J 9/0006 700/245 |
| 2015/0051527 | A1 | 2/2015 | Potter et al. | |
| 2015/0164660 | A1 | 6/2015 | Will et al. | |
| 2015/0321342 | A1* | 11/2015 | Smith | B25J 9/0009 74/490.03 |
| 2015/0336265 | A1* | 11/2015 | Choi | B25J 9/0006 414/4 |
| 2015/0366739 | A1* | 12/2015 | Endo | A61H 3/00 482/4 |
| 2016/0250094 | A1* | 9/2016 | Amundson | A61H 1/024 623/24 |
| 2016/0331625 | A1 | 11/2016 | Sankai et al. | |

FOREIGN PATENT DOCUMENTS

| | | |
|---|---|---|
| JP | 09-173398 A | 7/1997 |
| JP | 2007-307216 A | 11/2007 |
| JP | 2014-226373 A | 12/2014 |
| KR | 20-0458671 Y1 | 2/2012 |
| KR | 1020130045826 A | 5/2013 |
| KR | 10-1368817 B1 | 3/2014 |
| KR | 10-1486014 B1 | 1/2015 |
| WO | WO-2014093470 A1 | 6/2014 |
| WO | WO-2015115191 A1 | 8/2015 |

OTHER PUBLICATIONS

Extended European Search Report issued by the European Patent Office dated Mar. 22, 2017 for corresponding EP Patent Application No. 16163528.9.
Cara L. Lewis and Daniel P. Ferris, "Invariant hip moment pattern while walking with a robotic hip exoskeleton", Journal of Biomechanics, 44 (2011), pp. 789-793.
Hip Flexion Assist Device Powerpoint, MSHFAD.com, Becker Orthopedic International, pp. 1-23.
Stefano Carda, et al., "Efficacy of a Hip Flexion Assist Orthosis in Adults With Hemiparesis After Stroke", Journal of the American Physical Therapy Association, Physical Therapy, May 2012, vol. 92, No. 5, pp. 734-739.
Yasushi Ikeuchi et al., "Walking Assist Device with Bodyweight Support System", 2009 IEEE/RSJ International Conference on Intelligent Robots and Systems, Oct. 11-15, 2009, St. Louis, USA.
Freedom of Motion, "Walking Assist Device with Stride Management Assist" For those with weakened leg muscles who are still able to walk, Honda, The Power of Dreams, walkassist.honda.com, http://corporate.honda.com/innovation/walk-assist/StrideManagementAssist.
Freedom of Motion, "Walking Assist Device with Bodyweight Support Assist", For activities requiring extended standing or repetitive lower-body tasks, Honda, The Power of Dreams, walkassist.honda.com, http://corporate.honda.com/innovation/walk-assist/BodyweightSupportAssist.pdf.

\* cited by examiner

MOTION ASSISTANCE APPARATUS AND METHOD OF CONTROLLING THE SAME

CROSS-REFERENCE TO RELATED APPLICATION

This application claims under 35 U.S.C. § 119 to Korean Patent Application No. 10-2015-0115513, filed on Aug. 17, 2015, in the Korean Intellectual Property Office, the entire contents of which are incorporated herein by reference in its entirety.

BACKGROUND

1. Field

At least one example embodiment relates to a motion assistance apparatus and/or a method of controlling the same.

2. Description of the Related Art

With the onset of rapidly aging societies, a number of people may experience inconvenience and/or pain from joint problems. Thus, there may be a growing interest in motion assistance apparatuses enabling the elderly and/or patients having joint problems to walk with less effort. Furthermore, motion assistance apparatuses increasing muscular strength of human bodies may be desired for military purposes.

SUMMARY

Some example embodiments relate to a motion assistance apparatus.

In some example embodiment, the motion assistance apparatus may include a fixing module to be attached to a waist of a user, a driving module provided in the fixing module to provide a torque to assist a motion of the user, a supporting module connected to the driving module to support a portion of a circumference of a leg of the user, and a controller configured to control the driving module to provide a torque to maintain a close contact between the supporting module and the leg of the user while the user is not walking.

The supporting module may include a force transmitting frame of which one end portion is connected to the driving module and another end portion extends along the leg of the user, and a plate body connected to the force transmitting frame to support a rear side of the circumference of the leg of the user.

The supporting module may further include a wing disposed on a side of the leg of the user to extend from the plate body toward one side or both sides, and one end portion of the wing may be disposed not to overlap a front surface of the leg of the user based on a direction in which the force transmitting frame rotates.

The motion assistance apparatus may further include an elastic body configured to provide an elastic force to the supporting module in a direction in which the user proceeds in a state in which the user is standing erect.

The elastic body may include a first connector connected to the fixing module, and a second connector connected to the supporting module.

The elastic body may further include a hanging portion disposed between the first connector and the second connector and hung on one side of the fixing module or the supporting module.

The elastic body may be a torsion spring further including a winding portion wound over the driving module.

The elastic body may include a static load spring configured to provide a predetermined elastic torque irrespective of a rotation angle of the leg of the user.

An end portion of the supporting module may be disposed between a hip joint and a knee of the user to support a thigh of the user, and an additional driving module and an additional supporting module configured to assist a motion of another portion of the user may not be connected to the end portion of the supporting module.

The controller may be configured to control the driving module based on information received from at least one of an inertial sensor configured to measure angular information of an upper body of the user, an encoder configured to measure an angle between the upper body and a lower body of the user, a pressure sensor configured to measure a pressure applied by the leg of the user to the supporting module, and a strain gauge configured to measure a deformation of the supporting module.

Other example embodiments relate to a method of controlling a motion assistance apparatus including a fixing module to be attached to a waist of a user and a supporting module configured to support a leg of the user.

In some example embodiments, the method may include sensing leg rotation information of the user, determining a motion of the user based on the sensed leg rotation information, determining a necessary torque to be provided to the user based on the determined motion, determining a driving torque of a driving module configured to generate a motion assistance force, based on the necessary torque, and rotating the supporting module by driving the driving module with the determined driving torque. The supporting module may be connected to the driving module to support a rear surface of the leg of the user.

The determining of the necessary torque may include determining the necessary torque to be a predetermined motion assistance torque when a motion of the user is a flexion motion, determining the necessary torque to be a contact maintenance torque less than the motion assistance torque when the motion of the user is a stop motion, and determining the necessary torque to be "0" when the motion of the user is an extension motion.

The leg rotation information of the user may include at least one of an angular velocity of the leg of the user, a gait cycle of the user, a pressure applied to the supporting module, and a deformation degree of the supporting module.

The sensing may include measuring an angle of an upper body of the user, measuring a relative angle between the upper body and the leg of the user, determining an angle of the leg of the user based on the angle of the upper body and the relative angle, and determining the angular velocity of the leg of the user.

The determining of the motion may include determining the motion of the user to be a flexion motion when the angular velocity is less than a first set value, determining the motion of the user to be a stop motion when the angular velocity is greater than or equal to the first set value, and less than a second set value which is greater than the first set value, and determining the motion of the user to be an extension motion when the angular velocity is greater than or equal to the second set value.

The motion assistance apparatus may further include an elastic body configured to provide an elastic force to the supporting module in a direction in which the supporting module proceeds forward, and the determining of the driving torque may include determining the driving torque to be a value obtained by subtracting the elastic torque of the elastic body from the necessary torque.

Other example embodiments relate to a method of controlling a motion assistance apparatus including a fixing module to be attached to a waist of a user and a supporting module configured to support a leg of the user.

In some example embodiments, the method may include sensing leg rotation information of the user, determining a motion of the user based on the sensed leg rotation information, determining a driving torque of a driving module configured to generate a motion assistance force, based on the determined motion, and rotating the supporting module in one direction by driving the driving module with the determined driving torque. The supporting module may be connected to the driving module to support a rear surface of the leg of the user.

The motion assistance apparatus may further include an elastic body configured to provide an elastic force to the supporting module in a direction in which the supporting module proceeds forward.

The determining of the motion may include determining the motion of the user to be a flexion motion when an angular velocity of the leg of the user is less than a set value, and determining the motion of the user to not be the flexion motion when the angular velocity of the leg of the user exceeds the set value.

The determining of the driving torque may include determining the driving torque to be a predetermined motion assistance torque when the motion of the user is the flexion motion, and determining the driving torque to be "0" when the motion of the user is not the flexion motion.

Some example embodiments relate to a motion assistance apparatus.

In some example embodiments, the motion assistance apparatus includes a driver configured to generate a driving torque to assist motion of a leg of a user; a controller configured to instruct the driver to generate the driving torque; and a support configured to support a rear half of thigh of the user such that the support is configured to maintain a distance therebetween when the user is in an idle state.

In some example embodiments, the controller is configured to determine which gait state is associated with the user based on one of an angular velocity of the leg of the user, a current gait state of the user within a gait cycle, an amount of pressure applied to the support, and a degree the support is deformed In some example embodiments, the support is configured to provide less force to the thigh of the user, if the gait state of the user is an extension state in which the leg of the user is swinging front to back than when the gait state of the user is a flexion state in which the leg of the user is swinging back to front.

In some example embodiments, the controller is configured to determine the gait state by setting the gait state of the user as one of the flexion state, the idle state, and the extension state based on the angular velocity of the leg of the user, a lower threshold angular velocity associated with the idle state, and a upper threshold angular velocity associated with the idle state.

In some example embodiments, the controller is configured to instruct the driver to generate a motion assistance torque as the driving torque, if the gait state if the user is the flexion state, the motion assistance torque being a level of torque sufficient to lift the leg of the user.

In some example embodiments, the controller is configured to, instruct the driver to set the driving torque to zero, if the gait state of the user is one of (i) the extension state, and (ii) the idle state and an elastic force applied to the support is equal to or greater than a contact maintenance torque, the contact maintenance torque being a level of torque less than the level of the motion assistance torque and sufficient to maintain the distance between the support and the rear half of the thigh of the user, and instruct the driver to generate the contact maintenance torque as the driving torque, if the gait state of the user is the idle state and the elastic force applied to the support is less than the contact maintenance torque.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
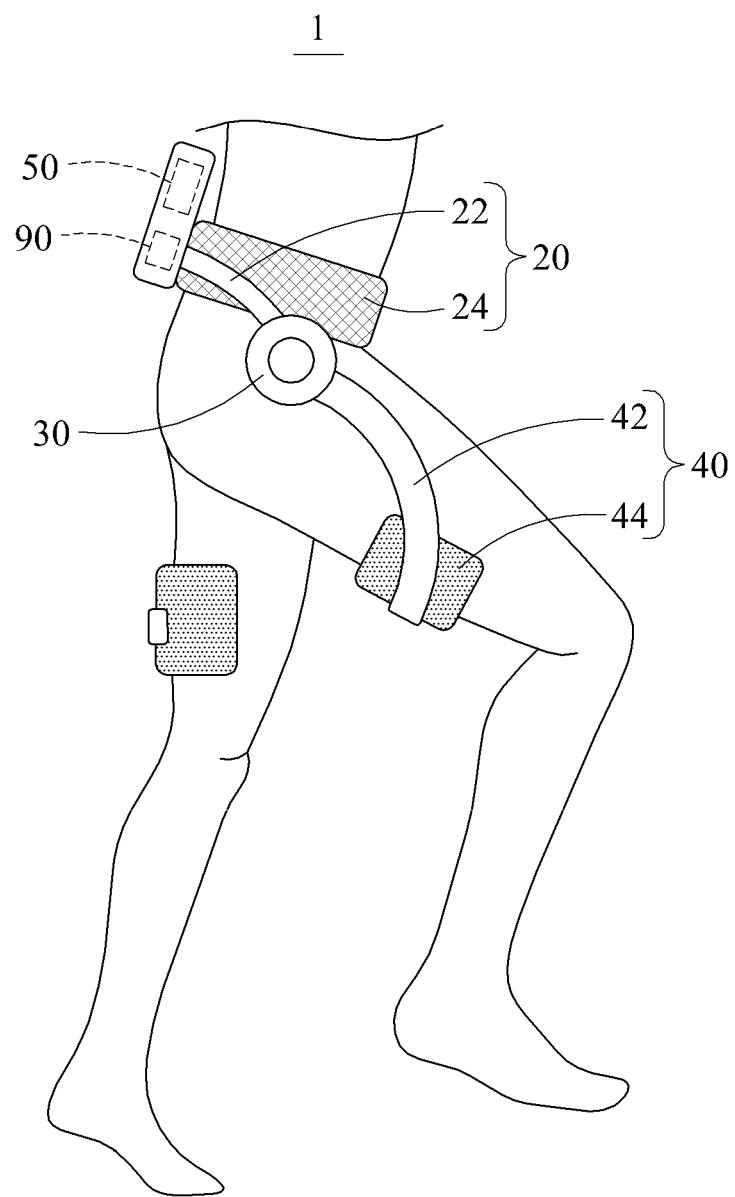
FIG. 1 is a side view illustrating a motion assistance apparatus according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as one computer processing device; however, one skilled in the art will appreciate that a hardware device may include multiple processing elements and multiple types of processing elements. For example, a hardware device may include multiple processors or a processor and a controller. In addition, other processing configurations are possible, such as parallel processors.

Various example embodiments will now be described more fully with reference to the accompanying drawings in which some example embodiments are shown. In the drawings, the thicknesses of layers and regions are exaggerated for clarity.

Figure 2:
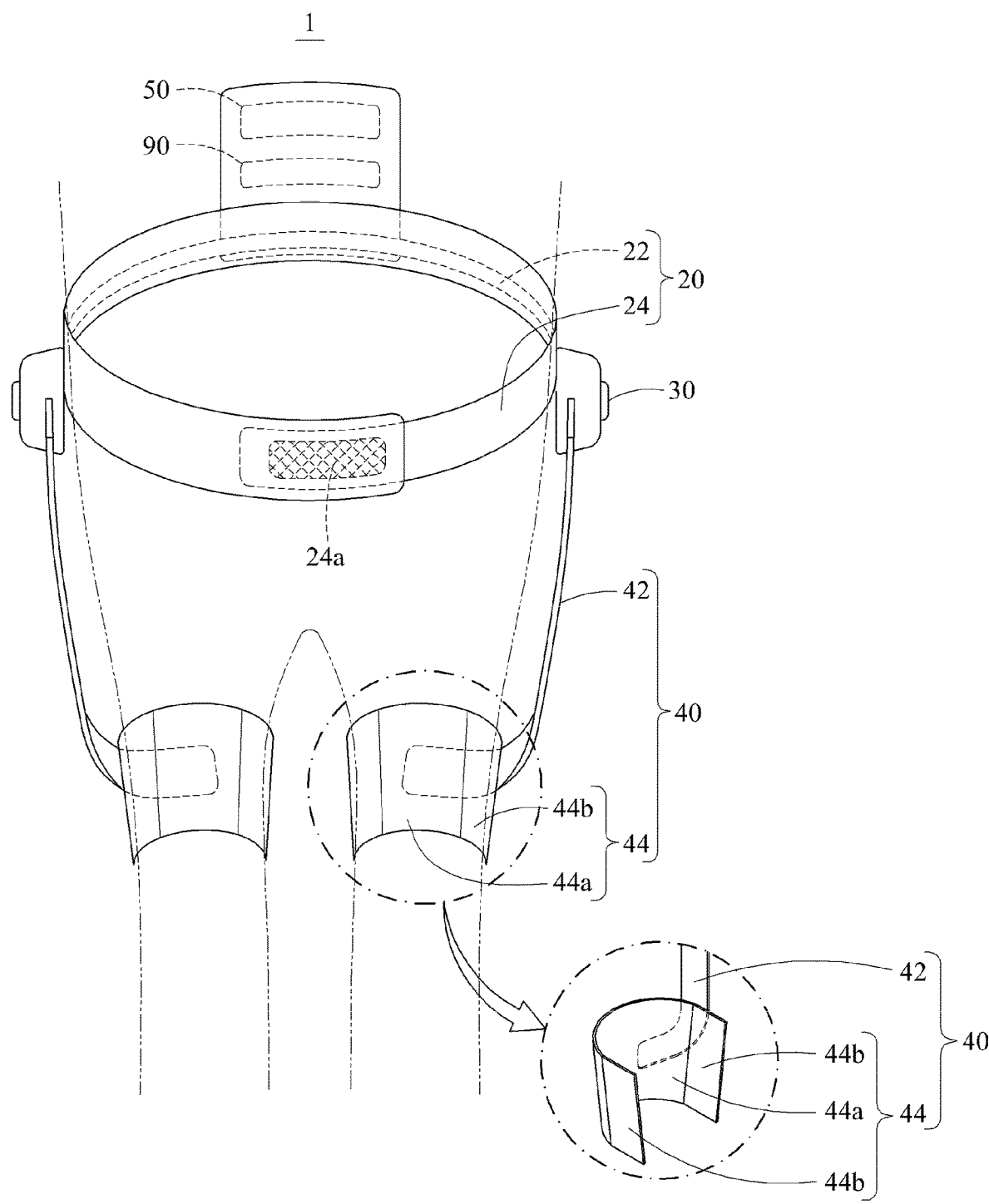
FIG. 2 is a front view illustrating a motion assistance apparatus according to at least one example embodiment.
Figure 3:
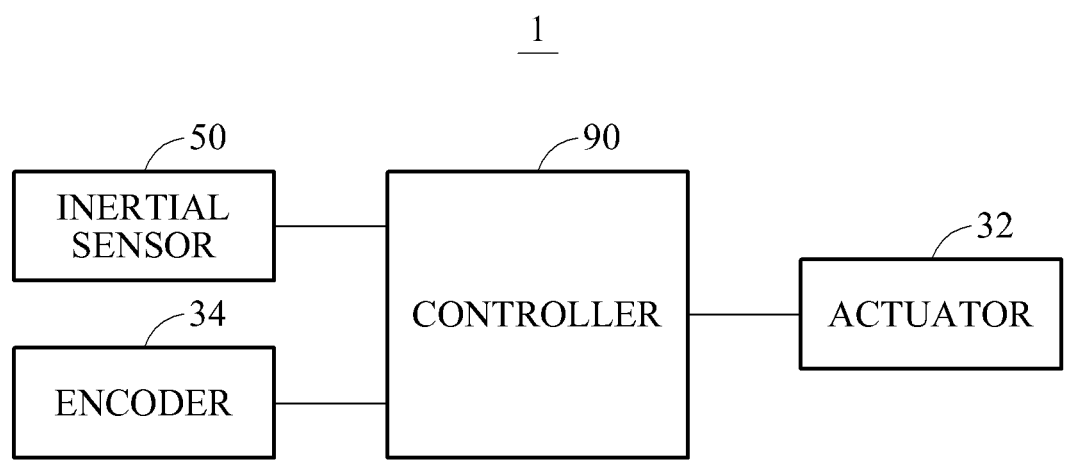
FIG. 3 is a block diagram illustrating a motion assistance apparatus according to at least one example embodiment.

FIG. 1 is a side view illustrating a motion assistance apparatus 1 according to at least one example embodiment, FIG. 2 is a front view illustrating the motion assistance apparatus 1 according to at least one example embodiment, and FIG. 3 is a block diagram illustrating the motion assistance apparatus 1 according to at least one example embodiment.

Referring to FIGS. 1 through 3, the motion assistance apparatus 1 may be worn by a user to assist a motion of the user.

In some example embodiments, the user may correspond to a human, an animal, or a robot. However, the user is not limited thereto. In addition, although FIG. 1 illustrates a case in which the motion assistance apparatus 1 assists motions of thighs of the user, the motion assistance apparatus 1 may assist a motion of any body part of the user. For example, the motion assistance apparatus 1 may also assist a motion of an upper body, for example, a hand, an upper arm, and a lower arm of the user. Further, the motion assistance apparatus 1 may assist a motion of another part of a lower body, for example, a foot, and a calf of the user.

Hereinafter, a case in which the motion assistance apparatus 1 assists motions of thighs of a human will be described. However, example embodiments are not limited thereto.

The motion assistance apparatus 1 may include a fixing module 20, a driving module 30, a supporting module 40, an inertial sensor 50, and a controller 90.

The fixing module 20 may be fixed to the user. The fixing module 20 may cover an outer surface of the user. For example, the fixing module 20 may be fixed to the sides of a waist of the user, and include a curved surface corresponding to a contact portion of the user. The fixing module 20 may include a fixing frame 22 configured to enclose at least a portion of the user, and a fixing band 24 connected to the fixing frame 22 and in close contact with the user.

For example, the fixing frame 22 may be formed using a rigid material, and the fixing band 24 may be formed using a flexible material. However, at least one example embodiment is not limited thereto. The fixing module 20 may include a single frame.

The fixing band 24 may include a fastening portion 24a that is detachable for ease of wearing. For example, the fastening portion 24a may be provided in a structure of a hook and loop fastener, a snap fastener, or a buckle fastener. However, example embodiments are not limited thereto.

The driving module 30 may be provided on one side of the fixing module 20 to provide a force or a torque to be transmitted to the supporting module 40. The driving module 30 may include an actuator 32 configured to receive a voltage or a current from a power supply and generate a rotation power, and an encoder 34 configured to measure an angle between an upper body and a lower body of the user. For example, the encoder 34 may measure the angle between the upper body and the lower body of the user by measuring an angle at which the actuator 32 rotates with respect to the fixing module 20.

Dissimilar to the drawings, the driving module 30 may also be connected to the supporting module 40 through a medium of a separate joint assembly. In this example, a power transmitting module configured to transmit a power from the driving module 30 to the joint assembly may be provided additionally. The power transmitting module may be a rotary body such as, for example, a gear, or a longitudinal member such as, for example, a wire, a cable, a string, a rubber band, a spring, a belt, and a chain.

The driving module 30 may be disposed on one or more sides of the fixing module 20. For example, the driving module 30 may be disposed at a position corresponding to one or more joint portions of the user, for example, one or more hip joint portions of the user. As described above, the driving module 30 may be connected to the supporting module 40 through a medium of the separate joint assembly. In this example, the joint assembly may be disposed at the joint portion of the user, for example, the hip joint portion of the user.

The supporting module 40 may rotate using the force or the torque provided from the driving module 30. The supporting module 40 may support a lower limb of the user, for example, a thigh of the user, and assist a motion of the lower limb. The supporting module 40 may support a rear portion of the thigh of the user, and transmit a force or a torque to move a leg of the user forward. For example, the supporting module 40 may support the rear portion of the thigh, but may not support a front portion of the thigh.

For example, as illustrated in the enlarged portion of FIG. 2, the supporting module 40 may not include a tightening portion configured to tighten the thigh. Instead, the supporting module 40 may include a band configured to enclose a front portion of the leg of the user. The band may include a flexible material such as, for example, fabric, silicon, and/or rubber. The band may prevent a separation of the leg of the user from the supporting module 40 while the driving module 30 is out of operation (or, alternatively, idle). Although a supporting band is provided, the band may not substantially transmit a force or a torque to move the leg of the user backward according to a control method to be described later. Unless otherwise disclosed, it should not be interpreted that the supporting module 40 should not include any component configured to enclose a thigh. The supporting module 40 may include a force transmitting frame 42, and a supporting plate 44.

The force transmitting frame 42 may transmit a force to a portion of the user. One end portion of the force transmitting frame 42 may be rotatably connected to the driving module 30, and another end portion of the force transmitting frame 42 may be connected to the supporting plate 44 to transmit a force to the supporting plate 44.

The supporting plate 44 may be connected to the other end portion of the force transmitting frame 42 to apply a force to a portion of the user. The supporting plate 44 may be disposed on a rear side of the thigh of the user to push the thigh of the user. In the foregoing structure, the supporting plate 44 may transmit a force to the thigh of the user in a direction in which the thigh of the user is pushed when the force transmitting frame 42 rotates forward; however, the supporting plate 44 may not transmit a force to the thigh of the user when the force transmitting frame 42 rotates backward. For example, in some example embodiments, the supporting plate 44 may transmit a force to the user in only one direction. Therefore, since the supporting plate 44 may not tighten the thigh of the user, a pressure that the user may experience may be alleviated and a wearability may increase. Further, the supporting plate 44 may support only the rear side of the thigh. Thus, the supporting plate 44 may reduce a force action point, when compared to a case in which the thigh is tightened, whereby a distortion of the entire supporting module 40 may be reduced. In addition, the supporting plate 44 may be simply structured, whereby the weight of the motion assistance apparatus 1 may be reduced. The supporting plate 44 may include a plate body 44a connected to the other end portion of the force transmitting frame 42, and one or more wings 44b configured to extend from one or more sides of the plate body 44a.

The plate body 44a may be disposed on a rear side of the user based on a direction in which the user proceeds. For example, the plate body 44a may be disposed on a rear surface of the thigh of the user.

The wing 44b may be disposed on a side portion of the user. For example, the wing 44b may be disposed on a side surface of the thigh of the user. The wing 44b may prevent a lateral separation of the thigh of the user. The wing 44b may be provided not to enclose a front surface of the thigh. In detail, an end portion of the wing 44b which is positioned at a longest distance from the plate body 44a may be disposed to not overlap the front surface of the thigh based on a direction in which the force transmitting frame 42 rotates. In the foregoing structure, the lateral separation of the thigh of the user may be prevented while the thigh of the user is not tightened.

The inertial sensor 50, for example, an inertial measurement unit (IMU), may measure angle information of the upper body when the user is walking. The angle information of the upper body measured by the inertial sensor 50 may be transmitted to the controller 90 and utilized to confirm rotation information of the leg.

The controller 90 may include a memory and a processor.

The memory may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

The processor may be implemented by at least one semiconductor chip disposed on a printed circuit board. The processor may be an arithmetic logic unit, a digital signal processor, a microcomputer, a field programmable array, a programmable logic unit, a microprocessor or any other device capable of responding to and executing instructions in a defined manner.

The processor may be programmed with instructions that configure the processor into a special purpose computer to perform the operations illustrated in one or more of FIGS. 4, 5, 8, 16, 18, and 20 to determine a motion of the user, and control the driving module 30 based on the determined motion. For example, the processor may adjust an amount of driving torque provided to the user via the supporting module 40 to maintain a distance between the support and a rear half of a thigh of the user based on whether the user is in an idle state and whether a static elastic force is provided to the support irrespective of the driving torque. Therefore the controller 90 may improve the functioning of the motion assistance apparatus 1 itself by reducing a force from the supporting module 40 against the thigh of the user generated when the user begins to walk forward from an idle state.

In some example embodiments, the controller 90 may determine an angle of the lower body of the user based on an angle of the upper body of the user sensed by the inertial sensor 50, and a relative angle between the upper body and the lower body of the user sensed by the encoder 34. Further, the controller 90 may determine whether the user is performing a flexion motion in which the leg rotates forward, whether the user is performing an extension motion in which the leg rotates backward, or whether the user is performing a stop motion in which the leg is stopped at a desired (or, alternatively, a predetermined) angle, based on a variation in the determined angle of the lower body of the user.

In another example, the controller 90 may determine whether the user is performing the flexion motion, the extension motion, or the stop motion by comparing a current gait pattern of the user to an input (or, alternatively, a pre-input) gait pattern of the user, for example, a gait cycle of the user.

However, example embodiments are not limited thereto. For example, the controller 90 may employ other methods to determine a motion of a user.

In some example embodiments, the motion assistance apparatus 1 may include one or more additional driving modules and/or supporting modules. For example, the supporting module 40 may extend to a knee, and an additional driving module may be provided in the supporting module 40 at a position corresponding to a knee joint. Further, an additional supporting module may be connected to the additional driving module. The additional supporting module may assist a motion of a calf of the user by supporting the calf of the user.

However, dissimilar to the foregoing, as shown in FIG. 1, the end portion of the supporting module 40 may be disposed between the hip joint and the knee of the user, and an additional driving module and an additional supporting module configured to assist a motion of another portion of the user may not be connected to the end portion of the supporting module 40. Through the foregoing simple structure, the overall weight of the motion assistance apparatus 1 may be reduced.

Figure 4:
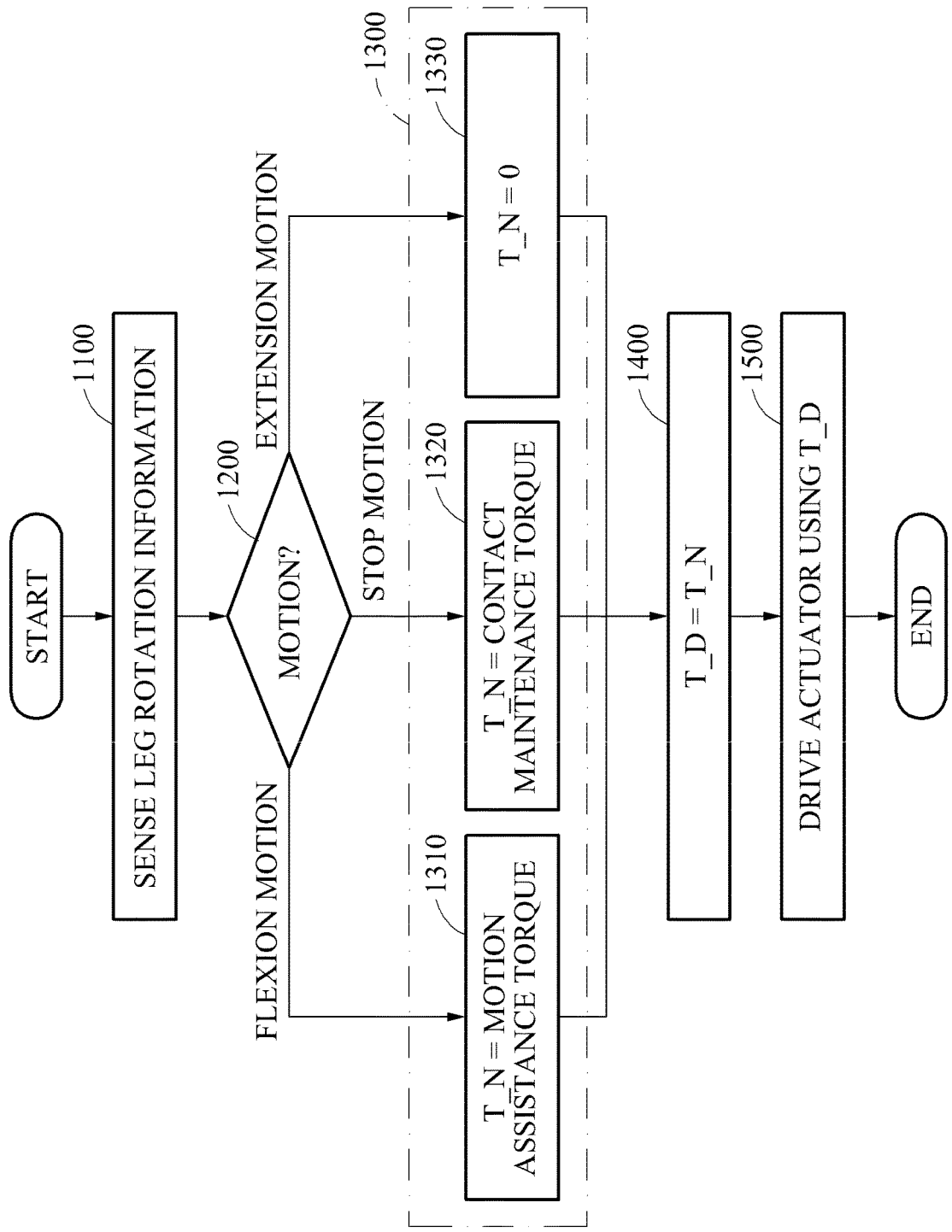
FIG. 4 is a flowchart illustrating a method of controlling a motion assistance apparatus according to at least one example embodiment.

FIG. 4 is a flowchart illustrating a method of controlling a motion assistance apparatus according to at least one example embodiment.

Referring to FIG. 4, the controller 90 may execute the method of controlling a motion assistance apparatus. For example, the controller may execute operation 1100 of sensing leg rotation information of a user, operation 1200 of determining a motion of the user based on the sensed leg rotation information, operation 1300 of determining a necessary (or, alternatively, a desired) torque T_N to be applied to the user based on the determined motion, operation 1400 of determining a driving torque T_D based on the determined necessary torque T_N, and operation 1500 of driving an actuator using the determined driving torque T_D.

In at least some example embodiments, the necessary torque T_N may be a sum of torques to be applied from outside to a lower body of the user. The driving torque T_D may be a torque generated by the driving module 30 and applied to the user. As illustrated in FIG. 4, in some example embodiments, the controller 90 may set the driving torque T_D to be identical to the necessary torque T_N. However, example embodiments are not limited thereto. For example, dissimilar to FIG. 4, the controller 90 may set the driving torque T_D in view of an effect of an external force other than the necessary torque T_N. Details of operations 1100 to 1500 will now be descried below.

In operation 1100, the controller 90 may sense the leg rotation information of the user directly or indirectly using a leg rotation information sensor. For example, a leg rotation information sensor that directly senses the leg rotation information of the user may include an inertial sensor attached directly to a leg of the user. A leg rotation information sensor that indirectly senses the leg rotation information of the user may include an inertial sensor configured to measure angle information of an upper body when the user is walking, an encoder configured to measure an angle between the upper body and a lower body of the user, a pressure sensor configured to measure a pressure applied by the leg of the user to a supporting module, and/or a strain gauge configured to measure a deformation of the supporting module. Operation 1100 will be discussed in more detail below with regards to FIGS. 5 to 7.

In operation 1200, the controller 90 may determine whether a motion of the user corresponds to flexion motion, stop motion or extension motion based on the sensed leg rotation information. Operation 1200 will be discussed in more detail below with regards to FIGS. 8 to 9B.

In operation 1300, the controller 90 may determine the necessary torque T_N based on whether the motion of the user corresponds to the flexion motion, for example, a state in which the leg of the user is rotating forward, the stop motion, for example, a state in which the leg of the user is not rotating, or the extension motion, for example, a state in which the leg of the user is rotating backward.

For example, in response to the controller 90 determining in operation 1200 that a motion of the user corresponds to a flexion motion, in operation 1310, the controller 90 may set the necessary torque T_N as a motion assistance torque. The motion assistance torque may refer to a torque that is preset to be a value that is sufficiently high for a supporting plate to lift the leg of the user, and applied in a direction in which the leg of the user is pushed. The user may receive the motion assistance torque and rotate the leg forward using less force. When the motion assistance torque is applied, the user may reduce use of a muscle of the user. Such reduction may reduce a load applied to a joint of the user, which is helpful to a patient suffering from a disease, for example, arthritis, and thus the disease may be mitigated and impeded.

In response to the controller 90 determining in operation 1200 that the motion of the user corresponds to the stop motion, in operation 1320, the controller 90 may set the necessary torque T_N as a contact maintenance torque. The contact maintenance torque may refer to a torque to be applied in a direction in which the leg of the user is pushed to maintain a contact between the supporting plate and a rear surface of the leg of the user, and may be preset. In detail, the contact maintenance torque is not a torque to directly rotate the leg of the user. A magnitude of the contact maintenance torque may be set to be less than a magnitude of the motion assistance torque. The contact maintenance torque may be set to be a sufficiently small value so that the user may not experience an excessive load from the contact maintenance torque when the user maintains a stop state. The contact maintenance torque may maintain a close contact between the thigh of the user and a supporting module of a motion assistance apparatus not including a thigh tightening portion at all times. Accordingly, when the leg of the user switches a motion from the stop motion to the flexion motion, a sudden slap of the supporting module on the thigh of the user may be prevented. In addition, without using the thigh tightening portion, information related to a motion state of the user, for example, information on a pressure applied between the thigh and the supporting module, may be confirmed.

In response to the controller 90 determining in operation 1200 that the motion of the user corresponds to the extension motion, in operation 1330, the controller 90 may determine the necessary torque T_N as "0". The supporting module supports the rear surface of the thigh of the user. Thus, when the leg of the user rotates backward, the close contact between the supporting module and the thigh may be maintained by a self-load of the supporting module although a separate torque is not provided. Accordingly, by setting a torque to be applied to the user to "0", a force that obstructs a backward rotation of the leg of the user may be minimized.

In operation 1400, the controller 90 may determine the driving torque T_D based on the necessary torque T_N determined in operation 1300.

For example, in some example embodiments, a torque is to be transmitted to the user entirely through the driving module, for example, when another component configured to transmit a torque to the user is not provided in addition to a driving module. Thus, the controller 90 may set the driving torque T_D to be a value identical to the necessary torque T_N.

In other example embodiments, when another component configured to transmit a torque to the user is provided in addition to the driving module, the controller 90 may set the driving torque T_D based on the necessary torque T_N and a torque of the other component.

Figure 5:
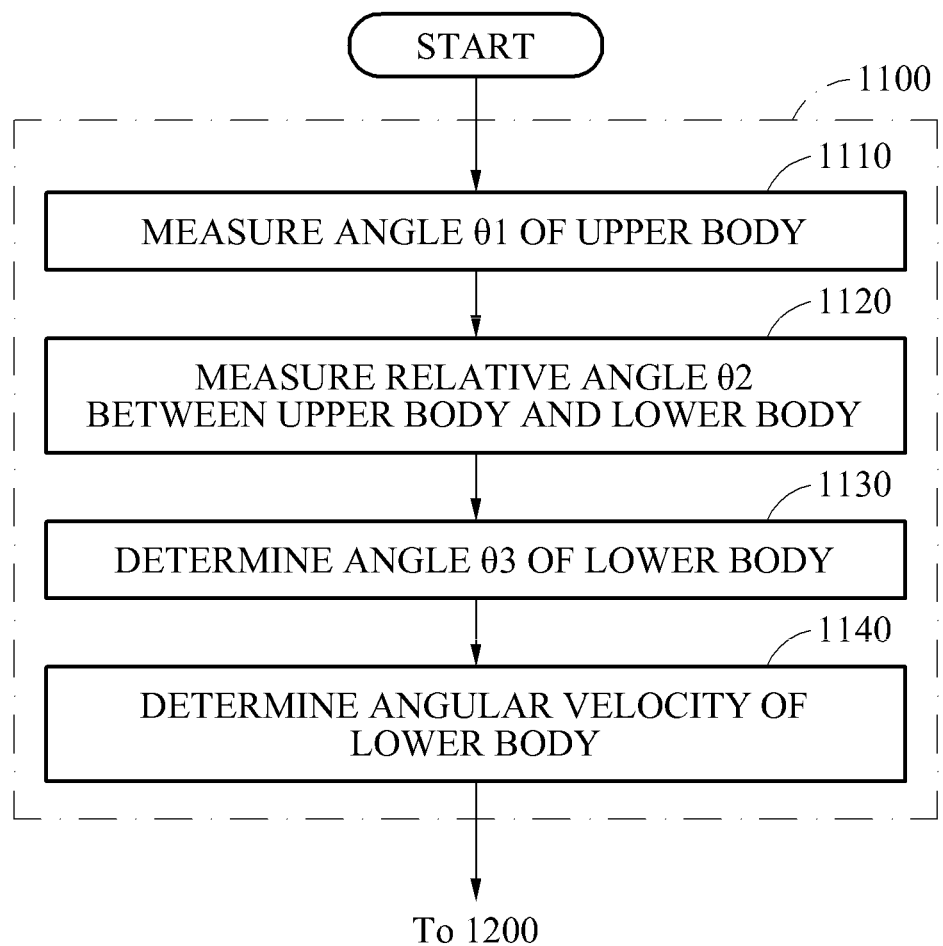
FIG. 5 is a flowchart illustrating an operation of sensing leg rotation information according to at least one example embodiment.
Figure 6:
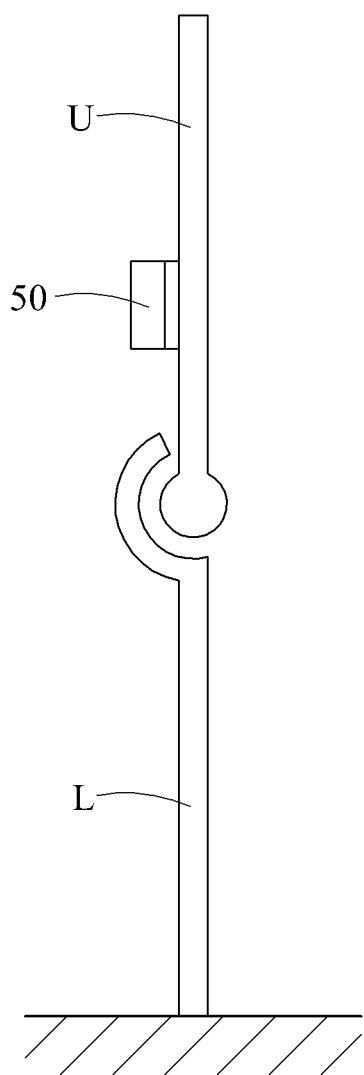
FIG. 6 illustrates a state in which a user is standing erect to describe an operation of sensing leg rotation information according to at least one example embodiment.
Figure 7:
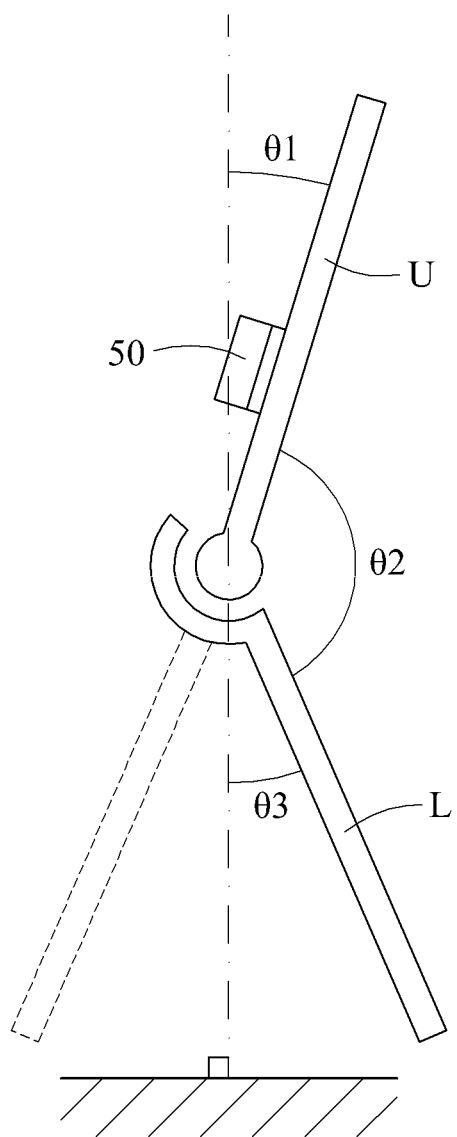
FIG. 7 illustrates a state in which a user is walking to describe an operation of sensing leg rotation information according to at least one example embodiment.

FIG. 5 is a flowchart illustrating operation 1100 of sensing leg rotation information according to at least one example embodiment, FIG. 6 illustrates a state in which a user is standing erect to describe operation 1100 of sensing leg rotation information according to at least one example embodiment, and FIG. 7 illustrates a state in which a user is walking to describe operation 1100 of sensing leg rotation information according to at least one example embodiment.

Referring to FIGS. 5 through 7, in executing operation 1100 of sensing leg rotation information, the controller 90 may execute operation 1110 of measuring an angle θ1 of an upper body of a user, operation 1120 of measuring a relative angle θ2 between the upper body and a lower body of the user, operation 1130 of determining an angle θ3 of the lower body of the user, and operation 1140 of determining an angular velocity of the lower body of the user.

In operation 1110, the controller 90 may, for example, measure the angle θ1 of the upper body U of the user based on a direction vertical to the ground. The controller 90 may measure the angle θ1 of the upper body U of the user based on information sensed by the inertial sensor 50 fixed to one side of the fixing module 20. For example, the inertial sensor 50 may include three accelerometers configured to measure rectilineal motions, and three gyroscopes configured to measure rotational motions.

In operation 1120, the controller 90 may, measure the angle θ2 between the upper body U and the lower body L, irrespective of a motion state of the user. For example, the controller 90 may measure the angle θ2 between the upper body U and the lower body L of the user based on information sensed by the encoder 34 fixed to one side of the fixing module 20 to measure a rotation angle of the supporting module 40 with respect to the fixing module 20. For example, the encoder 34 may be connected to a rotation axis of the actuator of the driving module 30.

In operation 1130, the controller 90 may determine the angle θ3 of the lower body L of the user based on a direction vertical to the ground, irrespective of the motion state of the user. For example, the controller 90 may determine the angle θ3 based on the two angles θ1 and θ2 respectively measured in operations 1110 and 1120.

In operation 1140, the controller 90 may determine the angular velocity of the lower body of the user based on a differential value of the angle θ3 determined in operation 1130 with respect to a time.

Example embodiments are not limited to the control method described above. For example, Operation 1100 may be performed using another method. For example, in other example embodiments, an inertial sensor may be attached directly to a leg of the user, and leg rotation information of the user, for example, an angular velocity of the leg, may be sensed based on information sensed by the attached inertial sensor.

Figure 8:
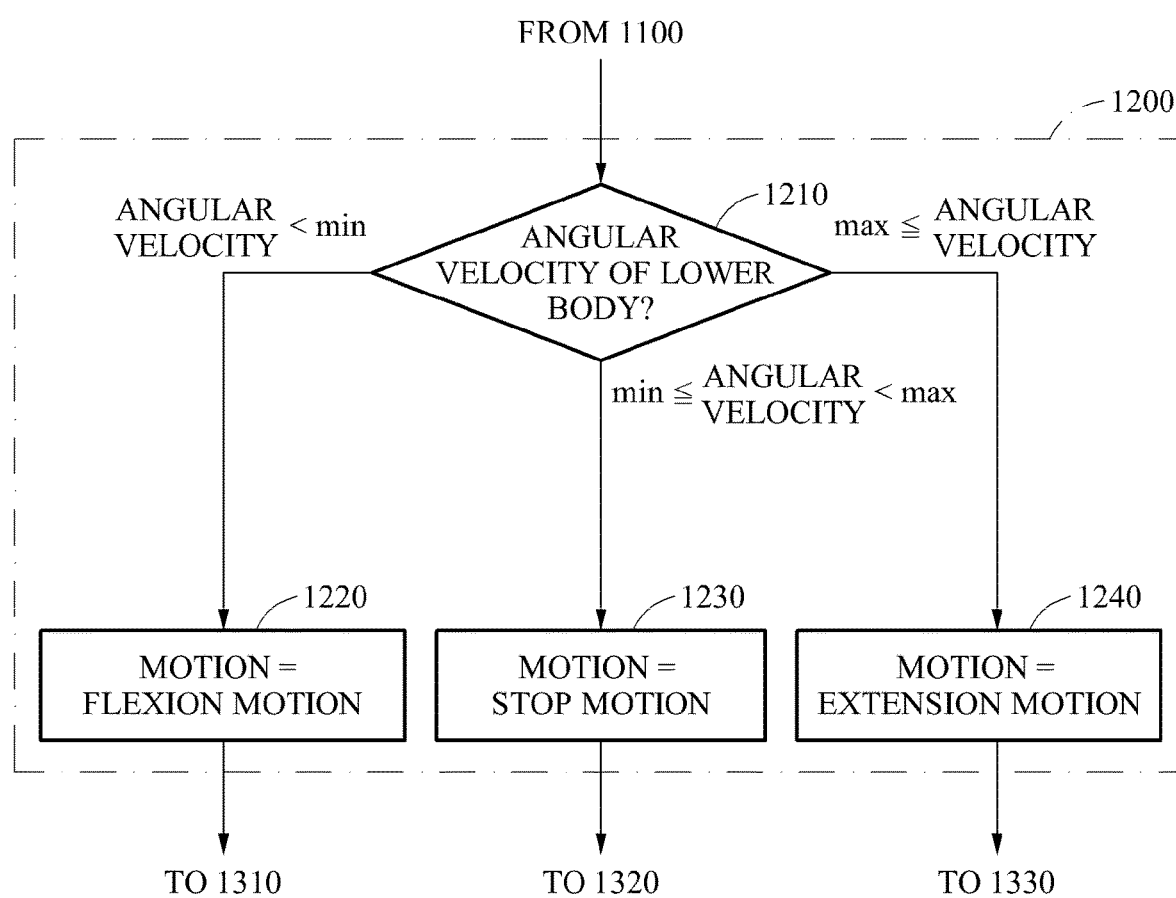
FIG. 8 is a flowchart illustrating an operation of determining a motion according to at least one example embodiment.
Figure 9A:
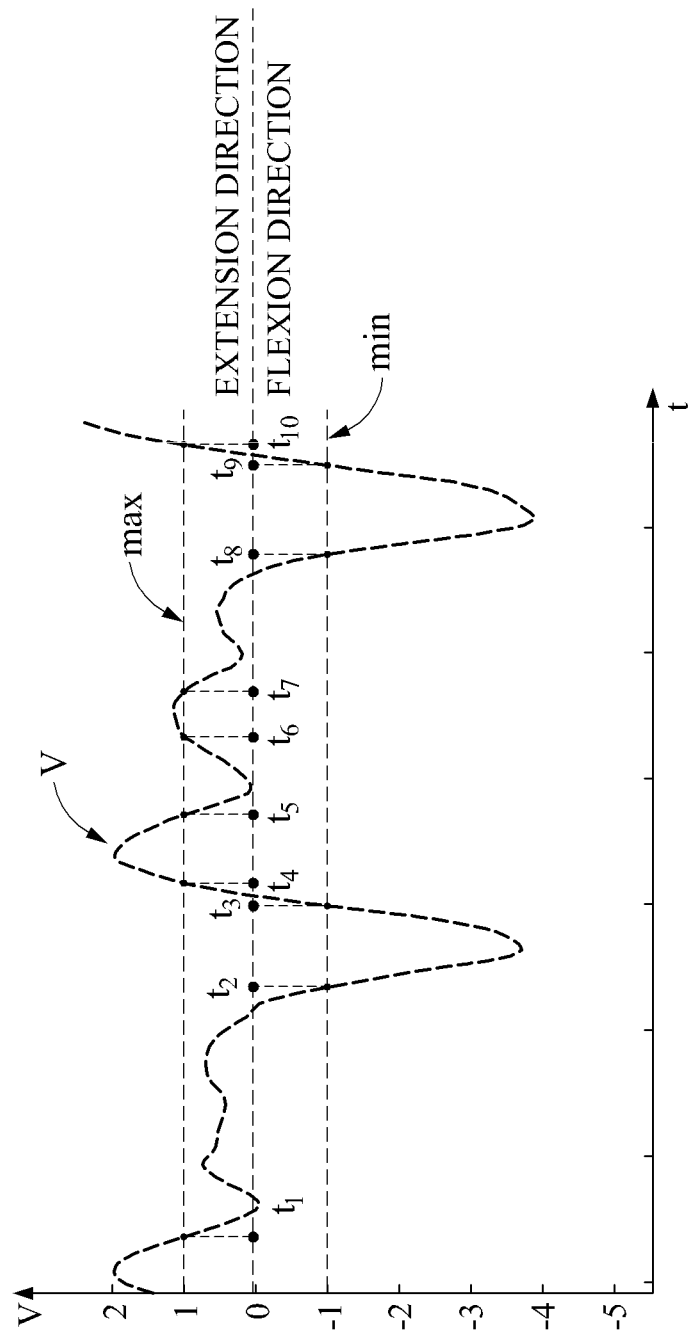
FIG. 9A is a graph illustrating a rotation speed of one leg of a user.
Figure 9B:
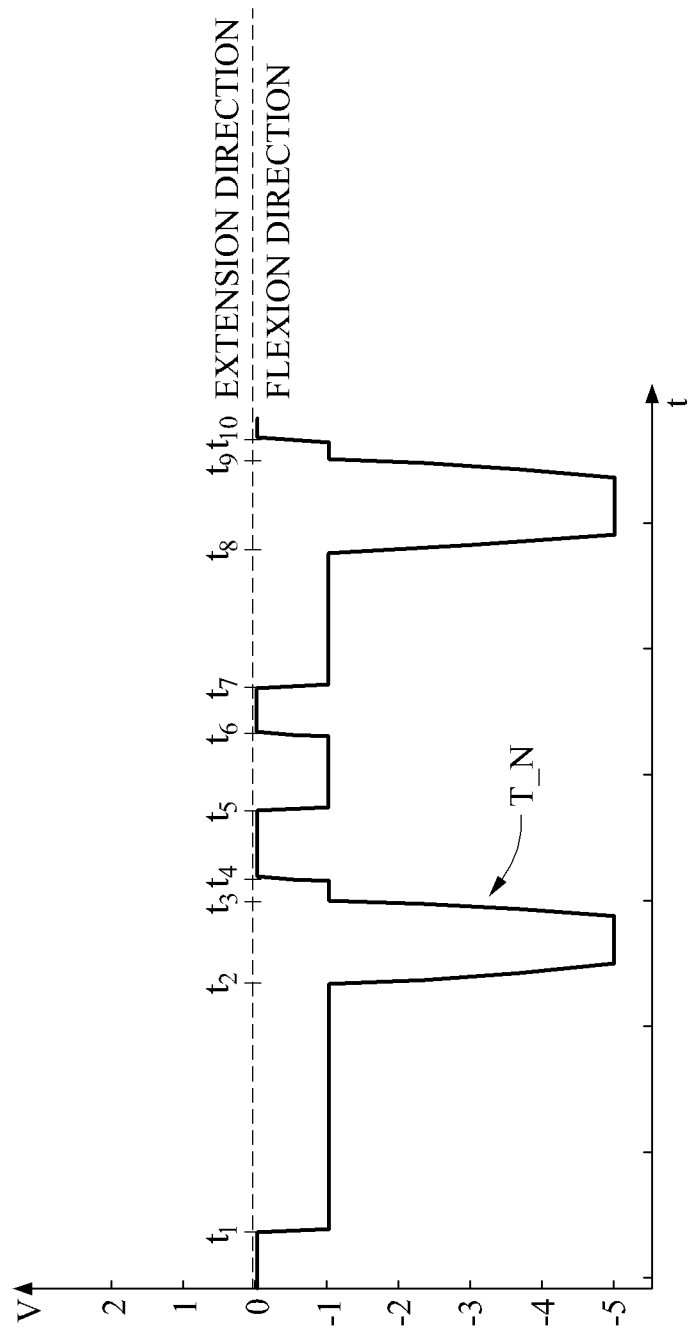
FIG. 9B is a graph illustrating a necessary torque determined through a method of controlling a motion assistance apparatus according to at least one example embodiment.

FIG. 8 is a flowchart illustrating operation 1200 of determining a motion according to at least one example embodiment, FIG. 9A is a graph illustrating a rotation speed of one leg of a user, and FIG. 9B is a graph illustrating a necessary torque determined through a method of controlling a motion assistance apparatus according to at least one example embodiment.

Referring to FIGS. 8 through 9B, in executing operation 1200 of determining a motion, the controller 90 may execute operation 1210 of comparing an angular velocity of a lower body of a user to at least one set value, and operations 1220, 1230, and 1240 of determining a motion based on a result of the comparing of operation 1210.

As illustrated in FIG. 8, the motion may be classified into three motions. The motion may include an extension motion associated with the user rotating a leg backward, a flexion motion associated with the user rotating the leg forward, and a stop motion associated with the user stopping rotating the leg rather than rotating the leg within a desired (or, alternatively, predetermined) range.

Here, the stop motion may be set to be a desired (or, alternatively, a predetermined) period including a period in which an angular velocity of a lower body of the user is exactly "0". In this example, an excessive load applied to a controller and a driving module in response to an excessive change in a control signal of the driving module may be prevented. Hereinafter, descriptions will be provided based on a condition that an angular velocity in a state in which the leg of the user rotates forward, for example, when the leg of the user moves in a flexion direction, is set to be a negative value, and an angular velocity in a state in which the leg of the user rotates backward, for example, when the leg of the user moves in an extension direction, is set to be a positive value. Meanwhile, signs of the angular velocity may be set reversely.

In operation 1210, the controller 90 may compare the angular velocity of the lower body of the user to a first set value ("min") and a second set value ("max") which is greater than the first set value. In detail, FIG. 9A illustrates a case in which the first set value is "−1", and the second set value is "1". In this example, the first set value and the second set value may be values having a unit of a torque, for example, Newton meter (Nm).

In operation 1220, if the controller 90 determines that the angular velocity of the lower body of the user is less than the first set value, the controller 90 may set a motion of the user as the flexion motion, and the controller 90 may determine a necessary torque T_N, for example, by performing operation 1310. In detail, in FIG. 9A, in a period between t2 and t3 and a period between t8 and t9 in which the angular velocity V of the lower body of the user is less than "−1", the motion of the user may be determined to be the flexion motion. In this example, as shown in FIG. 9B, a necessary torque T_N to be applied to the lower body of the user in the period between t2 and t3 and the period between t8 and t9 may be set to be a desired (or, alternatively, a predetermined) motion assistance torque.

In operation 1230, when the controller 90 determines that the angular velocity of the lower body of the user is greater than or equal to the first set value and less than the second set value, the motion of the user may be determined to be the stop motion, and the controller 90 may determine a necessary torque T_N, for example, by performing operation 1320. In detail, in FIG. 9A, in a period between t1 and t2, a period between t3 and t4, a period between t5 and t6, a period between t7 and t8, and a period between t9 and t10 in which the angular velocity V of the lower body of the user is greater than or equal to "−1" and less than "1", the controller 90 may determine the motion of the user to be the stop motion. In this example, as shown in FIG. 9B, in the corresponding periods, the controller 90 may apply a necessary torque to the lower body of the user as a desired (or, alternatively, a predetermined) contact maintenance torque.

In operation 1240, when the angular velocity of the lower body of the user is greater than or equal to the second set value, the controller 90 may determine the motion of the user to be the extension motion, and the controller 90 may determine a necessary torque T_N, for example, by performing operation 1330. In detail, in FIG. 9A, in a period between 0 and t1, a period between t4 and t5, a period between t6 and t7, and a period after t10 in which the angular velocity V of the lower body of the user is greater than or equal to "1", the motion of the user may be determined to be the extension motion. In this example, as shown in FIG. 9B, the controller 90 may set a necessary torque T_N to be applied to the lower body of the user in the corresponding periods to "0".

Dissimilar to the foregoing example, operation 1200 of determining a motion may include an operation of determining a motion with time based on a input (or, alternatively, a pre-input) gait cycle or a recent mean gait cycle confirmed in real time, rather than the angular velocity of the lower body.

Figure 10:
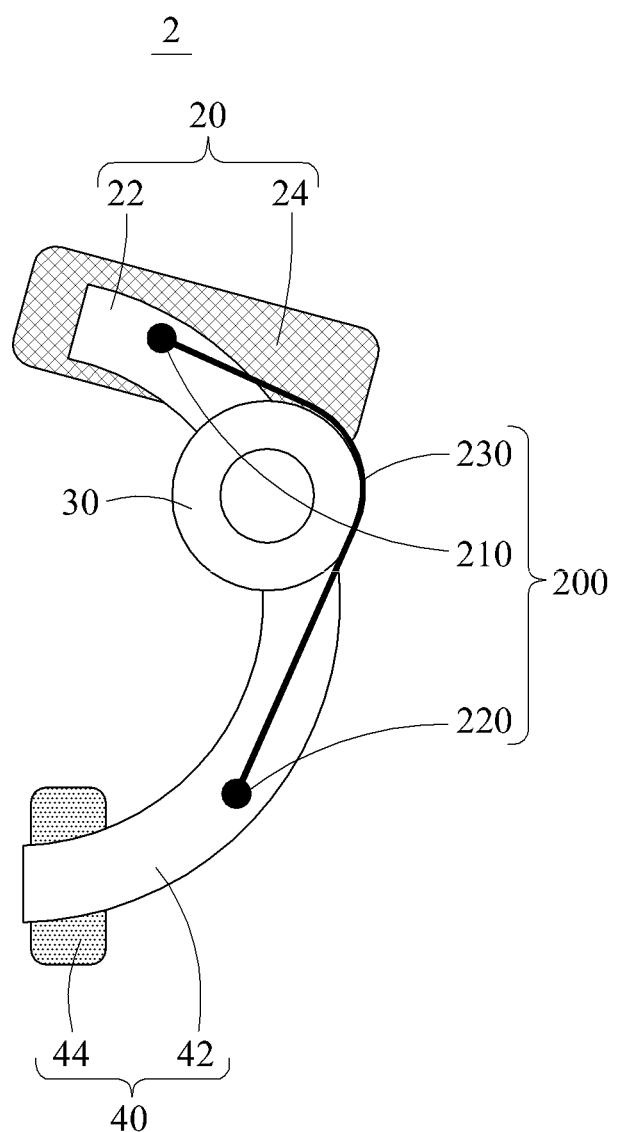
FIGS. 10 and 11 are views illustrating a motion assistance apparatus according to at least one example embodiment.
Figure 11:
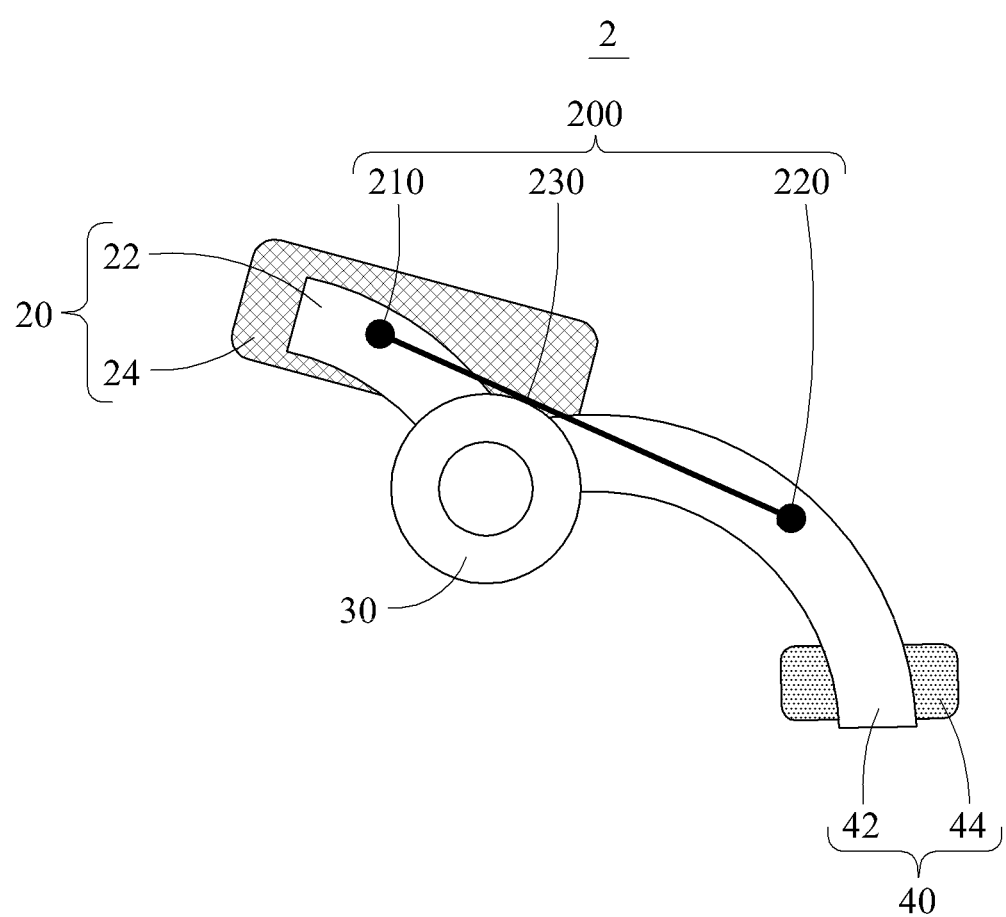

FIGS. 10 and 11 are views illustrating a motion assistance apparatus 2 according to at least one example embodiment. In detail, FIG. 10 illustrates the motion assistance apparatus 2 in a state in which a user is standing erect, and FIG. 11 illustrates the motion assistance apparatus 2 in a state in which a leg of the user rotates forward.

Referring to FIGS. 10 and 11, the motion assistance apparatus 2 may further include an elastic body 200 configured to provide an elastic force to the supporting module 40. The elastic body 200 may be, for example, a rubber band, or a spring. The elastic body 200 may include a first connector 210 connected to the fixing module 20, a second connector 220 connected to the supporting module 40, and a hanging portion 230 disposed between the first connector 210 and the second connector 220 and hung on one side of the fixing module 20 or the supporting module 40.

The first connector 210 may be connected to, for example, the fixing frame 22 of the fixing module 20. The second connector 220 may be connected to, for example, the force transmitting frame 42 of the support module 40. The elastic body 200 may be hung on, for example, the driving module 30. In detail, the elastic body 200 may be connected to the motion assistance apparatus 2 along the fixing frame 22 and the force transmitting frame 42. In the foregoing structure, the elastic body 200 may be disposed on a path on which the fixing module 20 and the force transmitting frame 42 extend. Thus, a space to be additionally secured for a deformation and a movement of the elastic body 200 may be minimized.

For example, the elastic body 200 may be disposed inside the fixing frame 22, the driving module 30, and the force transmitting frame 42. By the foregoing shape, damage or corrosion of the elastic body 200 resulting from an external impact or a contaminant may be prevented, whereby a lifespan of the elastic body 200 may increase. Further, a body or cloth of the user being shut during the deformation of the elastic body 200 may be prevented.

The elastic body 200 may provide the supporting module 40 with an elastic force in a direction in which the supporting module 40 rotates forward with respect to the fixing module 20, in detail, in a flexion direction, while the user is standing erect. The elastic body 200 may enable the supporting module 40 to be in close contact with the user, without driving the driving module 30, while the user is standing erect. In detail, energy to be used to drive the driving module 30 to generate a contact maintenance torque may be saved.

The elastic body 200 may include, for example, a static load spring. In this example, irrespective of an angle of the supporting module 40, a constant elastic torque may be generated by the elastic body 200 and thus, the driving module 30 may be controlled simply and precisely.

Figure 12:
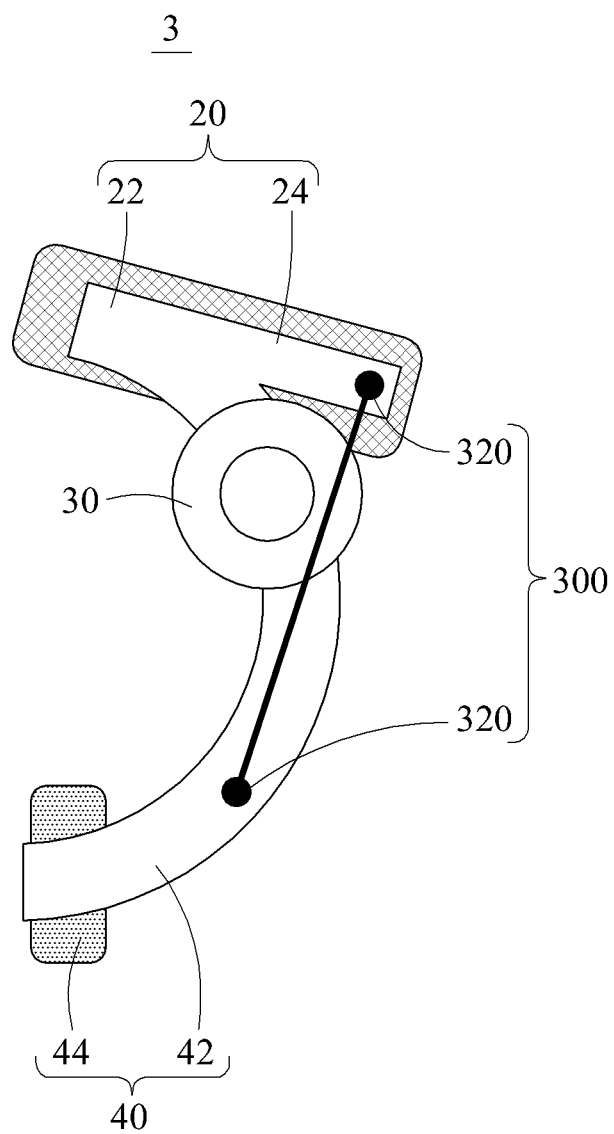
FIGS. 12 and 13 are views illustrating a motion assistance apparatus according to at least one example embodiment.
Figure 13:
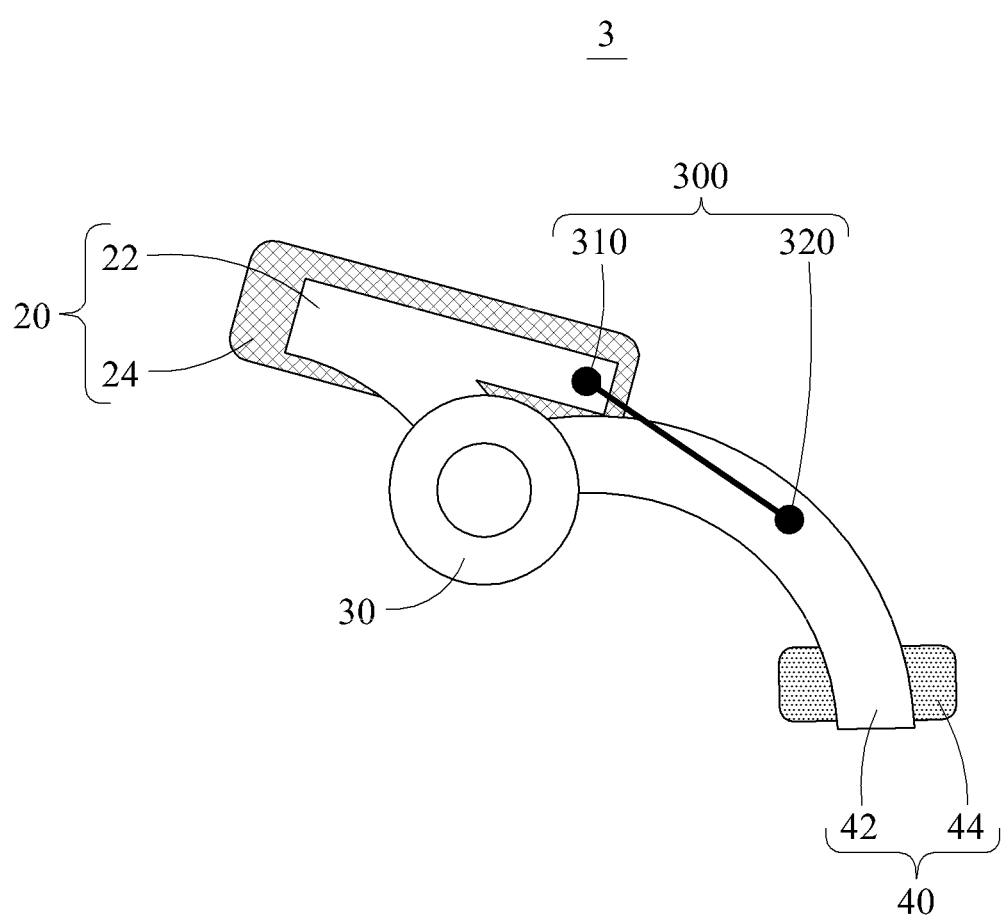

FIGS. 12 and 13 are views illustrating a motion assistance apparatus 3 according to at least one example embodiment. In detail, FIG. 12 illustrates the motion assistance apparatus 3 in a state in which a user is standing erect, and FIG. 13 illustrates the motion assistance apparatus 3 in a state in which a leg of the user rotates forward.

Referring to FIGS. 12 and 13, the motion assistance apparatus 3 may further include an elastic body 300 configured to provide an elastic force to the supporting module 40. The elastic body 300 may include a first connector 310 connected to the fixing module 20, and a second connector 320 connected to the supporting module 40. As illustrated in FIGS. 12 and 13, the elastic body 300 may not hang on the driving module 30.

Figure 14:
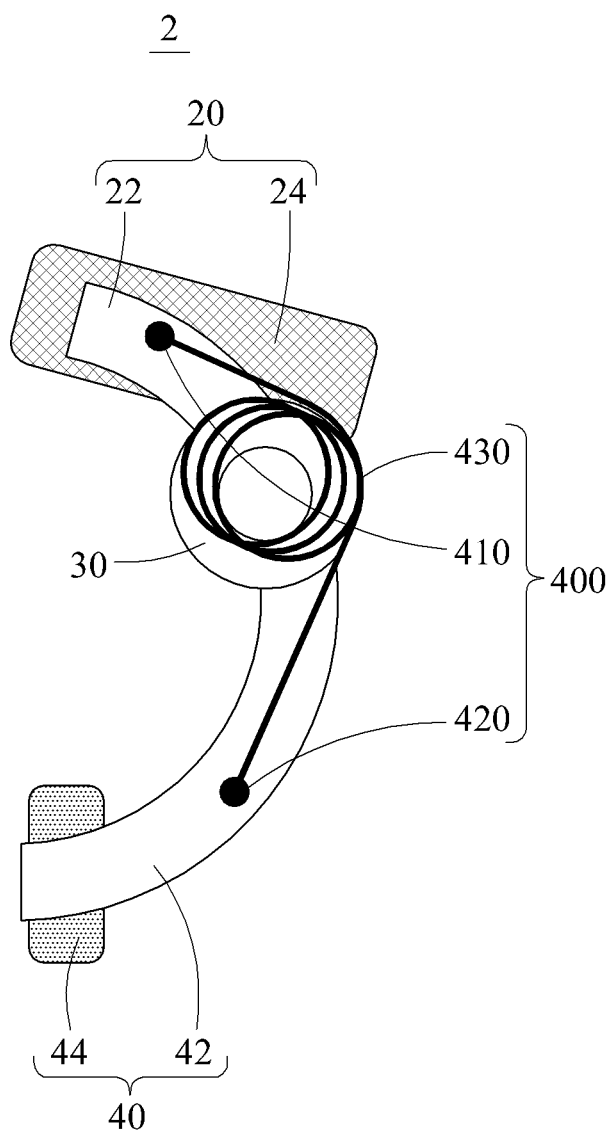
FIGS. 14 and 15 are views illustrating a motion assistance apparatus according to at least one example embodiment.
Figure 15:
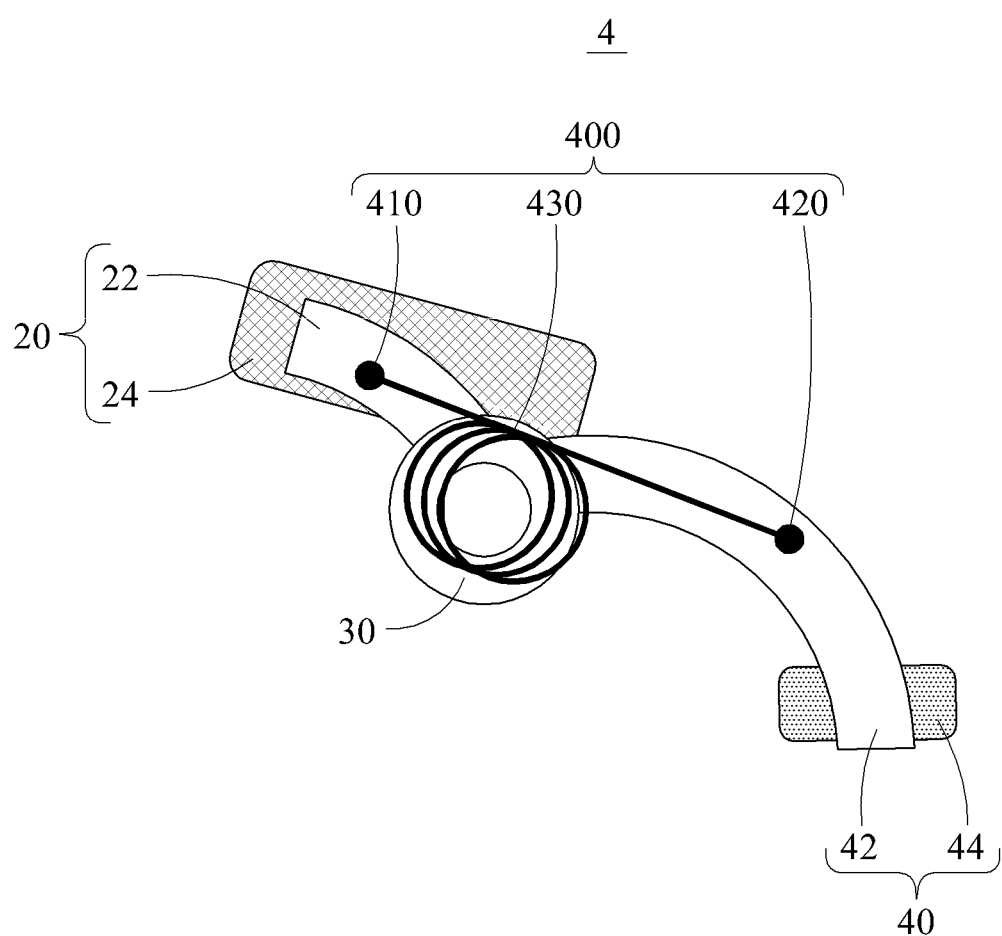

FIGS. 14 and 15 are views illustrating a motion assistance apparatus 4 according to at least one example embodiment. In detail, FIG. 14 illustrates the motion assistance apparatus 4 in a state in which a user is standing erect, and FIG. 15 illustrates the motion assistance apparatus 4 in a state in which a leg of the user rotates forward.

Referring to FIGS. 14 and 15, the motion assistance apparatus 4 may further include an elastic body 400 configured to provide an elastic force to the supporting module 40. The elastic body 400 may include a first connector 410 connected to the fixing module 20, a second connector 420 connected to the supporting module 40, and a winding portion 430 wound over the driving module 30. For example, the elastic body 400 may be a torsion spring configured to enclose the driving module 30. The motion assistance apparatus 4 may provide the user with a torque by the driving module 30 and a torque by the elastic body 400. The torque by the driving module 30 may be an active torque that changes based on a control signal of the controller 90. The torque by the elastic body 400 may be a passive torque, in detail, a torque determined (or, alternatively, predetermined) based on a specification of the elastic body 400 and a gait state of the user. When the driving module 30 and the elastic body 400 are used, a torque that changes suitably for a gait state of the user may be generated as described below.

Figure 16:
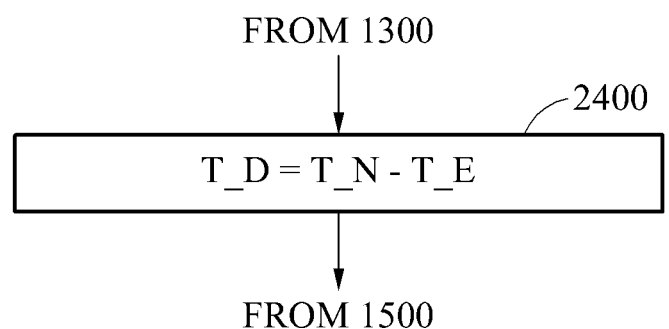
FIG. 16 is a flowchart illustrating a method of controlling a motion assistance apparatus according to at least one example embodiment.
Figure 17A:
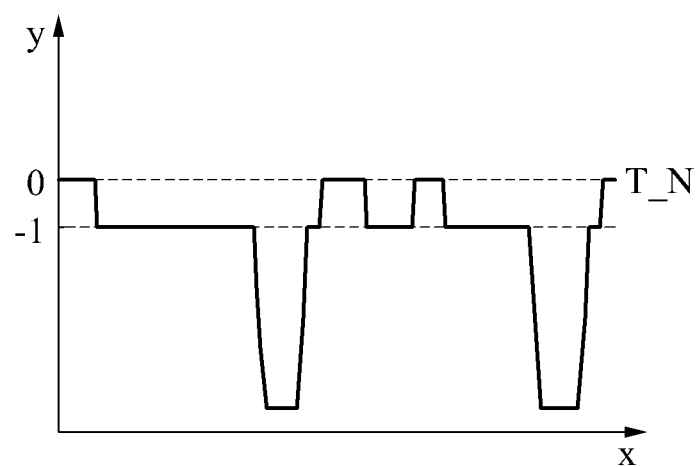
FIG. 17A is a graph illustrating a necessary torque determined through a method of controlling a motion assistance apparatus according to at least one example embodiment.
Figure 17B:
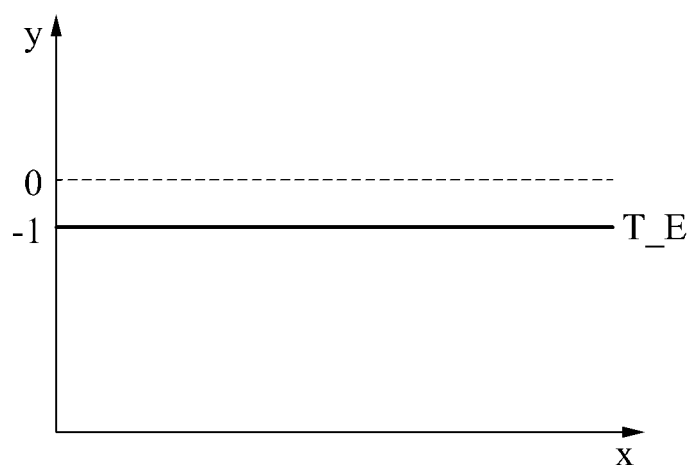
FIG. 17B is a graph illustrating an elastic torque determined through a method of controlling a motion assistance apparatus according to at least one example embodiment.
Figure 17C:
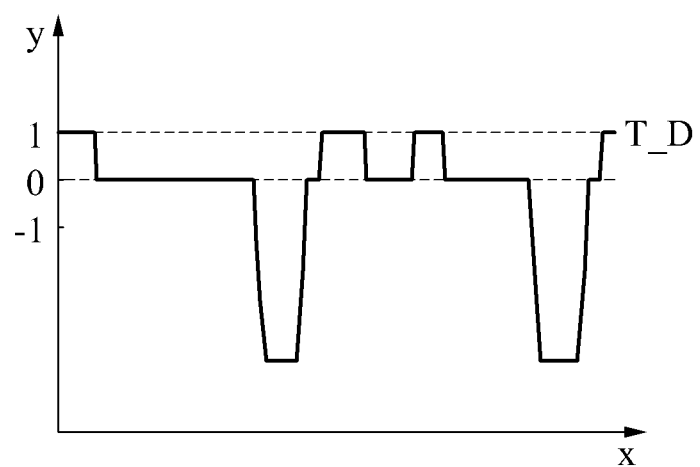
FIG. 17C is a graph illustrating a driving torque determined through a method of controlling a motion assistance apparatus according to at least one example embodiment.

FIG. 16 is a flowchart illustrating a method of controlling a motion assistance apparatus according to at least one example embodiment. FIG. 17A is a graph illustrating a necessary torque determined through the method of controlling a motion assistance apparatus according to at least one example embodiment, FIG. 17B is a graph illustrating an elastic torque determined through the method of controlling a motion assistance apparatus according to at least one example embodiment, and FIG. 17C is a graph illustrating a driving torque determined through the method of controlling a motion assistance apparatus according to at least one example embodiment. In FIGS. 17A through 17C, an axis Y indicates a magnitude of a torque, a positive direction of the axis Y indicates an extension direction, and a negative direction of the axis Y indicates a flexion direction.

Referring to FIGS. 16 through 17C, the method of controlling a motion assistance apparatus, hereinafter, the control method, may include operation 2400 of determining a driving torque T_D. For example, rather than performing operation 1400, the controller 90 may perform operation 2400 after operation 1300 of determining a necessary torque T_N is performed. In operation 2400, the controller 90 may determine the driving torque T_D based on the necessary torque T_N determined in operation 1300, and an elastic torque applied by an elastic body of the motion assistance apparatus to a lower body of a user.

FIG. 17B illustrates a case in which the elastic torque T_E has a constant value irrespective of a lapse of time or an angle of the lower body of the user. For example, when a static load spring is used as the elastic body, the elastic body may provide the user with a constant elastic torque T_E. In this example, the elastic torque T_E may be a value determined (or, alternatively, predetermined) based on a specification of the elastic body. In operation 2400, the controller 90 may determine a value obtained by subtracting the elastic torque T_E from the necessary torque T_N to be the driving torque T_D. In operation 1500, the controller may drive the actuator 32 using the driving torque T_D determined in operation 2400 such that an accurate necessary torque T_N may be provided to the user.

When considering a gait pattern of an average user, a time period corresponding to a stop motion may be longer than a remaining time period corresponding to a flexion motion or an extension motion. When an elastic body providing an elastic torque T_E identical to a contact maintenance torque is used, the driving torque T_D may be determined as shown in FIG. 17C. In this example, a driving module may not need to be driven during the time period corresponding to the stop motion. Thus, energy to be used for an operation of the driving module may be saved.

A torque applied in a positive direction of the axis Y of FIG. 17C may be a torque applied in the extension direction of the user. According to the foregoing control method, an elastic torque obstructing an extension motion of the user may be eliminated. To drive the driving module as shown in FIG. 17C, the driving module may rotate in both directions.

The elastic torque T_E may change based on an angle of the leg of the user. In this example, the controller 90 may sense the elastic torque T_E based on leg rotation information of the user, and determine a value obtained by subtracting the sensed elastic torque T_E from the necessary torque T_N to be the driving torque T_D. According to the foregoing control method, an accurate necessary torque T_N may be provided to the user by the elastic body and the driving module.

Figure 18:
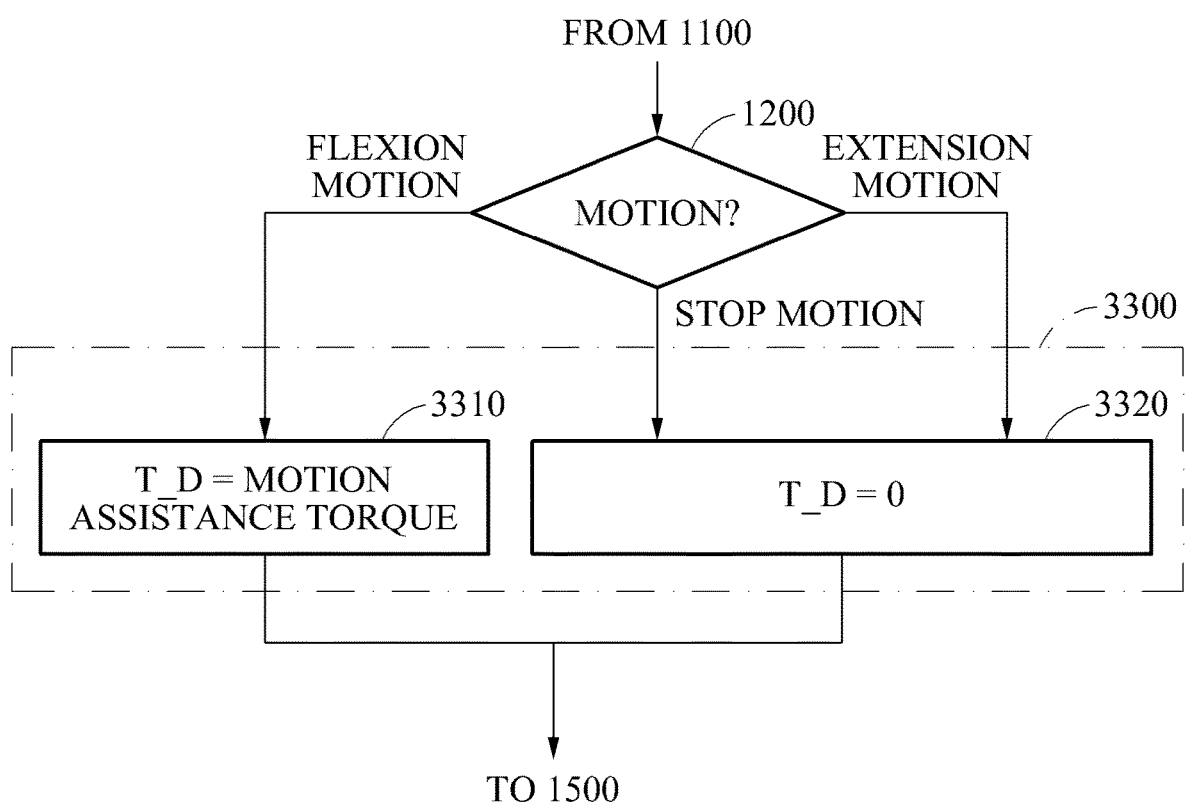
FIG. 18 is a flowchart illustrating a method of controlling a motion assistance apparatus according to at least one example embodiment.

FIG. 18 is a flowchart illustrating a method of controlling a motion assistance apparatus according to at least one example embodiment.

Referring to FIG. 18, rather than performing operation 1300 after the determination of the motion in operation 1200 (see FIG. 4), the controller 90 may perform operation 3300 to determine a driving torque T_D based on the determined motion. As discussed in more detail below, operation 3300 may include operations 3310 and 3320.

For example, in response to the controller 90 determining in operation 1200 that a motion of the user corresponds to a flexion motion, for example, a state in which the leg of the user is rotating forward, in operation 3310, the controller 90 may determine that the driving torque T_D is a motion assistance torque. The determination in operation 3310 may be similar to the determination in operation 1310 (see FIG. 4).

In response to the controller 90 determining in operation 1200 that the motion of the user does not correspond to the flexion motion, in operation 3320, the controller 90 may determine that the driving torque T_D is "0". For example, when the controller 90 determines that the motion corresponds to a stop motion or an extension motion, the controller 90 may determine that the driving T_D is "0". In a case of the stop motion or the extension motion, a close contact between a supporting module and a thigh may be maintained by a self-load of an elastic body or the supporting module. In this example, a driving module may not need to be driven during a time period corresponding to the stop motion or the extension motion and thus, energy to be used for an operation of the driving module may be saved.

According to the foregoing control method, a motion may be assisted by rotating the driving module in one direction only. In detail, a motion may be assisted using a driving module configured to generate a unidirectional torque. Further, the motion assistance apparatus may be controlled more simply, whereby a response of the motion assistance apparatus may increase and an error resulting from a complexity of the control method may be reduced.

Figure 19:
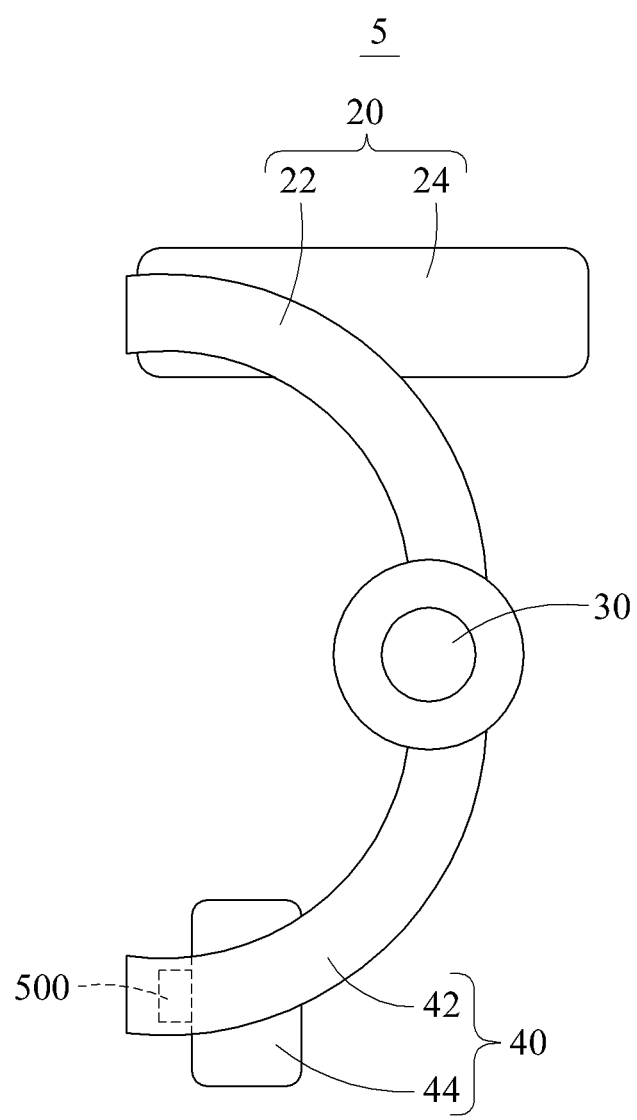
FIG. 19 is a view illustrating a motion assistance apparatus according to at least one example embodiment.
Figure 20:
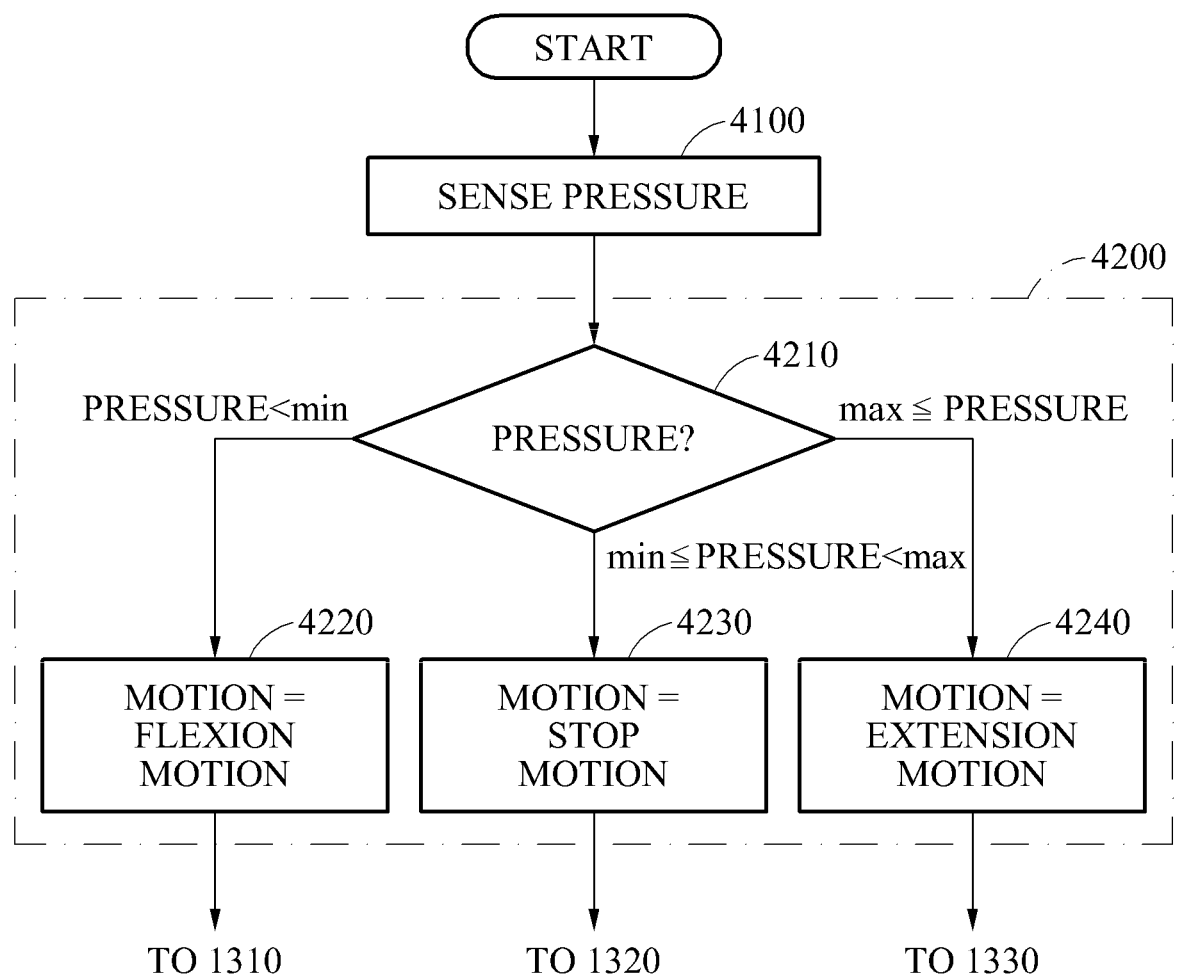
FIG. 20 is a flowchart illustrating a method of controlling a motion assistance apparatus according to at least one example embodiment.

FIG. 19 is a view illustrating a motion assistance apparatus 5 according to at least one example embodiment, and FIG. 20 is a flowchart illustrating a method of controlling the motion assistance apparatus 5 according to at least one example embodiment.

Referring to FIGS. 19 and 20, the motion assistance apparatus 5 may further include a pressure sensor 500 configured to measure a pressure applied by a leg of a user to the supporting module 40. The pressure sensor 500 may be disposed in the supporting module 40. For example, the pressure sensor 500 may be disposed between the force transmitting frame 42 and the supporting plate 44.

Referring to FIGS. 4 and 20, in a method of controlling the motion assistance apparatus 5, rather than performing operations 1100, 1200 and 1300, the controller 90 may perform operation 4100 to sense leg rotation information of the user, and operation 4200 to determine a motion of the user based on the sensed leg rotation information.

In operation 4100, the controller 90 may obtain the leg rotation information of the user based on a pressure sensed by the pressure sensor 500.

In operation 4200, the controller 90 may determine the motion based on the pressure sensed by the pressure sensor 500. Operation 4200 may include operations 4210, 4220, 4230 and 4240.

For example, in operation 4210, the controller 90 may compare the pressure sensed by the pressure sensor 500 to at last one set value, and perform one of operations 4220, 4230, and 4240 to determine a motion based on a result of the comparing of operation 4210.

More specifically, in operation 4210, the controller 90 may compare the sensed pressure to a first set value min and a second set value max which is greater than the first set value. In some example embodiments, the first set value and the second set value may be values having a unit of a pressure, for example, pascal (Pa). However, example embodiments are not limited thereto.

When the controller 90 determines, in operation 4210, that the pressure sensed by the pressure sensor 500 is less than the first set value min, in operation 4220, the controller 90 may determine that the leg of the user is performing flexion motion in which the leg of the user moves in a direction away from the supporting module 40, and, therefore, the controller 90 may determine a necessary torque T_N, for example, by performing operation 1310.

When the controller 90 determines, in operation 4210, that the pressure sensed by the pressure sensor 500 is greater than or equal to the first set value min and less than the second set value max, in operation 4230, the controller 90 may determine that the leg of the user is performing stop motion in which the leg of the user provides a pressure to the supporting module 40 within a desired (or, alternatively, a predetermined) range, and, therefore, the controller 90 may determine the necessary torque T_N, for example, by performing operation 1320.

When the controller 90 determines, in operation 4210, that the pressure sensed by the pressure sensor 500 is greater than or equal to the second set value max, in operation 4240, the controller 90 may determine that the leg of the user is performing extension motion in which the leg of the user moves toward the supporting module 40, and, therefore, the controller 90 may determine the necessary torque T_N, for example, by performing operation 1330.

In summary, the controller 90 may sense the leg rotation information of a user and/or determine a motion of the user indirectly using the foregoing method, without directly measuring an angle or an angular velocity of the leg of the user.

Figure 21:
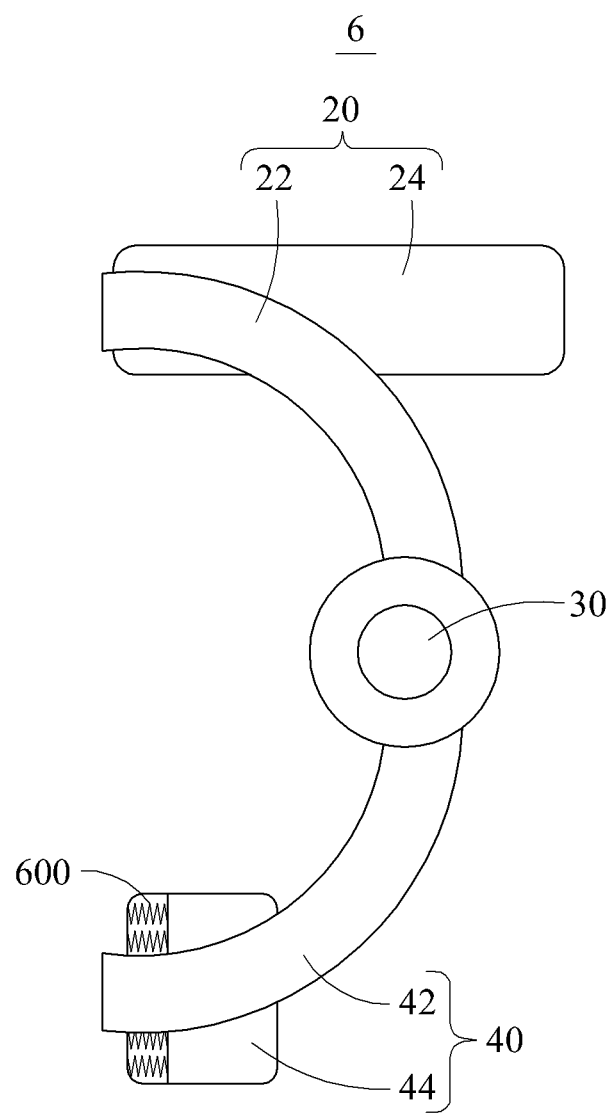
FIG. 21 is a view illustrating a motion assistance apparatus according to at least one example embodiment.

FIG. 21 is a view illustrating a motion assistance apparatus 6 according to at least one example embodiment.

Referring to FIG. 21, the motion assistance apparatus 6 may further include a strain gauge 600 configured to measure a deformation of the supporting module 40. The strain gauge 600 may be disposed in the supporting module 40. For example, the strain gauge 600 may be disposed in an elastic member provided in the supporting plate 44 to measure a deformation rate of the elastic member. The strain gauge 600 may be disposed in the force transmitting frame 42 to measure a deformation rate of the force transmitting frame 42.

The supporting module 40 may be deformed in proportion to a force or a pressure applied between a lower body of the user and the supporting module 40. Thus, the controller 90 may sense the leg rotation information using the strain gauge 600, and determine a motion of the user based on the sensed leg rotation information, as described above. Detailed descriptions thereof will be omitted for conciseness.

The units and/or modules described herein may be implemented using hardware components and software components. For example, the hardware components may include microphones, amplifiers, band-pass filters, audio to digital converters, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A motion assistance apparatus comprising:
a fixing device to be attached to a waist of a user;
a driver associated with the fixing device, the driver configured to generate a torque to assist a walking motion of the user;
a support including a force transmitting frame connected to the driver, the support configured to support a portion of a circumference of a leg of the user; and
a controller configured to control the driver to generate the torque such that the torque urges the support to maintain close contact between the support and the leg of the user when the leg of the user is stalled based on information from at least one sensor while the user is stopped at rest and standing erect in an idle state rather than performing the walking motion.

2. The motion assistance apparatus of claim 1, wherein the force transmitting frame has a first end portion and a second end portion, the first end portion of the force transmitting frame connected to the driver and the second end portion extending along the leg of the user; and the support further comprises:
a plate body connected to the force transmitting frame, the plate body configured to support a rear side of the circumference of the leg of the user.

3. The motion assistance apparatus of claim 2, wherein the support further comprises:
a wing configured extending from one or more sides of the plate body toward a side of the leg of the user such that the support does not overlap a front surface of the leg of the user based on a direction in which the force transmitting frame rotates.

4. The motion assistance apparatus of claim 1, further comprising:
an elastic body configured to provide an elastic force to the support in a direction in which the user walks.

5. The motion assistance apparatus of claim 4, wherein the elastic body comprises:
a first connector connected to the fixing device; and
a second connector connected to the support.

6. The motion assistance apparatus of claim 5, wherein a middle portion of the elastic body between the first connector and the second connector is configured to hang on one side of the fixing device or the support.

7. The motion assistance apparatus of claim 5, wherein the elastic body comprises:
a torsion spring including a winding portion wound over the driver.

8. The motion assistance apparatus of claim 5, wherein the elastic body comprises:
a static load spring configured to provide a same elastic torque irrespective of an amount of extension of the static load spring in response to increases in a rotation angle of the leg of the user.

9. The motion assistance apparatus of claim 1, wherein an end portion of the support is configured to support a thigh of the user between a hip joint and a knee of the user, and
an additional driver and an additional support configured to assist a motion of another portion of the user are not connected to the end portion of the support.

10. The motion assistance apparatus of claim 1, wherein the at least one sensor includes at least one of:
an inertial sensor configured to measure angular information of an upper body of the user,
an encoder configured to measure an angle between the upper body and a lower body of the user,
a pressure sensor configured to measure a pressure applied by the leg of the user to the support, and
a strain gauge configured to measure a deformation of the support.

11. A motion assistance apparatus comprising:
a driver configured to generate a driving torque to assist motion of a leg of a user;
a controller configured to instruct the driver to generate the driving torque; and
a support including a force transmitting frame connected to the driver and a plate body configured to support a rear half of thigh of the user, wherein
the controller controls the driver to generate the driving torque such that the driving torque urges the support to maintain a distance between the support and the rear half of the thigh of the user when the leg of the user is stalled based on information from at least one sensor while the user is not performing the motion and stopped at rest and standing erect in an idle state.

12. The motion assistance apparatus of claim 11, wherein the controller is configured to determine which gait state is associated with the user based on one of an angular velocity of the leg of the user, a current gait state of the user within a gait cycle, an amount of pressure applied to the support, and a degree the support is deformed.

13. The motion assistance apparatus of claim 12, wherein the controller is configured to instruct the driver to generate the driving torque such that the support provides less force to the thigh of the user, in response to the gait state of the user being an extension state in which the leg of the user is swinging front to back than when the gait state of the user is a flexion state in which the leg of the user is swinging back to front.

14. The motion assistance apparatus of claim 13, wherein the controller is configured to determine the gait state by setting the gait state of the user as one of the flexion state, the idle state, and the extension state based on the angular velocity of the leg of the user, a lower threshold angular velocity associated with the idle state, and an upper threshold angular velocity associated with the idle state.

15. The motion assistance apparatus of claim 13, wherein the controller is configured to instruct the driver to generate a motion assistance torque as the driving torque, in response to the gait state of the user being the flexion state, the motion assistance torque being a level of torque sufficient to lift the leg of the user.

16. The motion assistance apparatus of claim 15, wherein the controller is configured to,
instruct the driver to set the driving torque to zero, in response to the gait state of the user being one of (i) the extension state, and (ii) the idle state and an elastic torque applied to the support by an elastic body is equal to or greater than a contact maintenance torque, the contact maintenance torque being a level of torque less than the level of the motion assistance torque while maintaining the distance between the support and the rear half of the thigh of the user, and instruct the driver to generate the contact maintenance torque as the driving torque, in response to the gait state of the user being the idle state and the elastic torque applied to the support is less than the contact maintenance torque.

* * * * *